United States Patent
Bock et al.

(10) Patent No.: US 6,358,959 B1
(45) Date of Patent: Mar. 19, 2002

(54) POLYAZANAPHTHALENONE DERIVATIVES USEFUL AS ALPHA 1A ADRENOCEPTOR ANTAGONISTS

(75) Inventors: Mark G. Bock, Hatfield; Michael A. Patane, Harleysville; Thomas G. Steele, West Point, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/481,991

(22) Filed: Jan. 11, 2000

Related U.S. Application Data
(60) Provisional application No. 60/117,255, filed on Jan. 26, 1999.

(51) Int. Cl.[7] ..................... C07D 239/80; A61K 31/517
(52) U.S. Cl. ................... 514/255.05; 514/259; 544/286
(58) Field of Search ..................... 544/286; 514/255.05, 514/259

(56) References Cited

U.S. PATENT DOCUMENTS

| | | | |
|---|---|---|---|
| 4,661,491 A | 4/1987 | Regnier | 514/260 |
| 5,389,631 A | 2/1995 | Claremon et al. | 514/221 |
| 5,620,993 A | 4/1997 | Patane et al. | 514/321 |
| 5,661,163 A | 8/1997 | Patane et al. | 514/331 |
| 5,807,856 A | 9/1998 | Bock et al. | 514/252 |
| 5,922,722 A | 7/1999 | Bock et al. | 514/255 |

FOREIGN PATENT DOCUMENTS

| | | |
|---|---|---|
| EP | 0 748 800 | 12/1996 |
| WO | WO 92/00073 | 1/1992 |
| WO | WO 92/16213 | 10/1992 |
| WO | WO 94/08040 | 4/1994 |
| WO | WO 94/10989 | 5/1994 |
| WO | WO 94/22829 | 10/1994 |
| WO | WO 96/40135 | 12/1996 |
| WO | WO 96/40136 | 12/1996 |
| WO | WO 97/14846 | 4/1997 |
| WO | WO 97/17969 | 5/1997 |
| WO | WO 97/42956 | 11/1997 |
| WO | WO 98/57632 | 12/1998 |
| WO | WO 98/57638 | 12/1998 |
| WO | WO 98/57639 | 12/1998 |
| WO | WO 98/57640 | 12/1998 |
| WO | WO 98/57641 | 12/1998 |
| WO | WO 98/57642 | 12/1998 |

OTHER PUBLICATIONS

Nagarathnam et al., "Design, Synthesis and Evaluation of Dihydropyrimidinones as Alpha 1A Selective Antagonists: 1. Identification of SNAP 5582 as a Novel Lead", Abstract No. 082, 214th ACS National Meeting, Las Vegas, NV Sep. 1997.

Nagarathnam et al., "Design, Synthesis and Evaluation of Dihydropyrimidinones as Alpha 1A Selective Antagonists: 2. Structure–Activity Relationship of SNAP 5582 Analogs", Abstract No. 083, 214th ACS National Meeting, Las Vegas, NV Sep. 1997.

Marzabadi et al., "Design, Synthesis and Evaluation of Dihydropyrimidinones as Alpha 1A Selective Antagonists: 3. Modification of the Piperidine Moiety", Abstract No. 084, 214th ACS National Meeting, Las Vegas, NV Sep. 1997.

Lagu et al., "Design, Synthesis and Evaluation of Dihydropyrimidinones as Alpha 1A Selective Antagonists: 4. Dihydropyrimidinone–Fused Lactones", Abstract No. 085, 214th ACS National Meeting, Las Vegas, NV Sep. 1997.

Michel et al., "Classification of Alpha 1a Adrenoceptor Subtypes", Naunyn–Schmiedeberg's Arch Pharmacol (1995), 352: 1–10.

Primary Examiner—Mukund J. Shah
Assistant Examiner—Hong Liu
(74) Attorney, Agent, or Firm—Baerbel R. Brown; Catherine D. Fitch; Kenneth R. Walton

(57) ABSTRACT

Dihydro-polyazanaphthalen-2-one compounds (e.g., dihydroquinazolin-2-one and dihydropteridin-2-one derivatives) and pharmaceutically acceptable salts thereof are disclosed. The synthesis of these compounds and their use as alpha 1a adrenergic receptor antagonists is also described. One application of these compounds is in the treatment of benign prostatic hyperplasia. These compounds are selective in their ability to relax smooth muscle tissue enriched in the alpha 1a receptor subtype without at the same time inducing hypotension. One such tissue is found surrounding the urethral lining. Therefore, one utility of the instant compounds is to provide acute relief to males suffering from benign prostatic hyperplasia, by permitting less hindered urine flow. Another utility of the instant compounds is provided by combination with a human 5-alpha reductase inhibitory compound, such that both acute and chronic relief from the effects of benign prostatic hyperplasia can be achieved.

28 Claims, No Drawings

POLYAZANAPHTHALENONE DERIVATIVES USEFUL AS ALPHA 1A ADRENOCEPTOR ANTAGONISTS

CROSS REFERENCE TO RELATED APPLICATIONS

This application claims the benefit of U.S. Provisional Application No. 60/117,255 filed Jan. 26, 1999.

FIELD OF THE INVENTION

This invention relates to polyazanaphthalen-2-one derivatives (e.g., quinazolin-2-one and pteridin-2-one derivatives) and pharmaceutically acceptable salts thereof, their synthesis, and their use as alpha 1a adrenoceptor antagonists. More particularly, the compounds of the present invention are useful for treating benign prostatic hyperplasia (BPH).

References are made throughout this application to various publications, the disclosures of which are hereby incorporated by reference in their entireties, in order to more fully describe the state of the art to which this invention pertains.

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors bind norepinephrine more strongly than epinephrine and much more strongly than the synthetic compound isoproterenol. The binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into alpha 1, alpha 2, $\beta_1$, and $\beta_2$ subtypes. Functional differences between alpha 1 and alpha 2 receptors have been recognized, and compounds which exhibit selective binding between these two subtypes have been developed.

For a general background on the alpha adrenergic receptors, the reader's attention is directed to Robert R. Ruffolo, Jr., α-*Adrenoreceptors: Molecular Biology, Biochemistry and Pharmacology*, (*Progress in Basic and Clinical Pharmacology* series, Karger, 1991), wherein the basis of alpha 1/alpha 2 subclassification, the molecular biology, signal transduction (G-protein interaction and location of the significant site for this and ligand binding activity away from the 3'-terminus of alpha adrenergic receptors), agonist structure-activity relationships, receptor functions, and therapeutic applications for compounds exhibiting alpha-adrenergic receptor affinity was explored.

The cloning, sequencing and expression of alpha receptor subtypes from animal tissues has led to the subclassification of the alpha 1 receptors into alpha 1d (formerly known as alpha 1a or 1a/1d), alpha 1b and alpha 1a (formerly known as alpha 1c) subtypes. Each alpha 1 receptor subtype exhibits its own pharmacologic and tissue specificities. The designation "alpha 1a" is the appellation recently approved by the IUPHAR Nomenclature Committee for the previously designated "alpha 1c" cloned subtype as outlined in the 1995 Receptor and Ion Channel Nomenclature Supplement (Watson and Girdlestone, 1995). The designation alpha 1a is used throughout this application to refer to this subtype. At the same time, the receptor formerly designated alpha 1a was renamed alpha 1d. The new nomenclature is used throughout this application. Stable cell lines expressing these alpha 1 receptor subtypes are referred to herein; however, these cell lines were deposited with the American Type Culture Collection (ATCC) under the old nomenclature. For a review of the classification of alpha 1 adrenoceptor subtypes, see, Michel et al., *Naunyn-Schmiedeberg's Arch. Pharmacol.* (1995), 352:1–10.

The differences in the alpha adrenergic receptor subtypes have relevance in pathophysiologic conditions. Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra. Concomitantly, the increased noradrenergic innervation of the enlarged prostate leads to an increased adrenergic tone of the bladder neck and urethra, further restricting the flow of urine through the urethra.

In benign prostatic hyperplasia, the male hormone 5alpha-dihydrotestosterone has been identified as the principal culprit. The continual production of 5α-dihydrotestosterone by the male testes induces incremental growth of the prostate gland throughout the life of the male. Beyond the age of about fifty years, in many men, this enlarged gland begins to obstruct the urethra with the pathologic symptoms noted above.

The elucidation of the mechanism summarized above has resulted in the recent development of effective agents to control, and in many cases reverse, the pernicious advance of BPH. In the forefront of these agents is Merck & Co., Inc.'s product PROSCAR® (finasteride). The effect of this compound is to inhibit the enzyme testosterone 5-α reductase, which converts testosterone into 5α-dihydrotesterone, resulting in a reduced rate of prostatic enlargement, and often reduction in prostatic mass.

The development of such agents as PROSCAR® bodes well for the long-term control of BPH. However, as may be appreciated from the lengthy development of the syndrome, its reversal also is not immediate. In the interim, those males suffering with BPH continue to suffer, and may in fact lose hope that the agents are working sufficiently rapidly.

In response to this problem, one solution is to identify pharmaceutically active compounds which complement slower-acting therapeutics by providing acute relief. Agents which induce relaxation of the lower urinary tract tissue, by binding to alpha 1 adrenergic receptors, thus reducing the increased adrenergic tone due to the disease, would be good candidates for this activity. Thus, one such agent is alfuzosin, which is reported in EP 0 204597 to induce urination in cases of prostatic hyperplasia. Likewise, in WO 92/00073, the selective ability of the R(+) enantiomer of terazosin to bind to adrenergic receptors of the alpha 1 subtype was reported. In addition, in WO 92/16213, combinations of 5α-reductase inhibitory compounds and alpha1-adrenergic receptor blockers (terazosin, doxazosin, prazosin, bunazosin, indoramin, alfuzosin) were disclosed. However, no information as to the alpha 1d, alpha 1b, or alpha 1a subtype specificity of these compounds was provided as this data and its relevancy to the treatment of BPH was not known. Current therapy for BPH uses existing non-selective alpha 1 antagonists such as prazosin (Minipress, Pfizer), Terazosin (Hytrin, Abbott) or doxazosin mesylate (Cardura, Pfizer). These non-selective antagonists suffer from side effects related to antagonism of the alpha 1d and alpha 1b receptors in the peripheral vasculature, e.g., hypotension and syncope.

The relatively recent cloning of the human alpha 1a adrenergic receptor (ATCC CRL 11140) and the use of a screening assay utilizing the cloned human alpha 1a receptor has enabled identification of compounds which specifically interact with the human alpha 1a adrenergic receptor. For further description, see WO 94/08040 and WO 94/10989. As disclosed in the instant patent disclosure, a cloned human alpha 1a adrenergic receptor and a method for identifying compounds which bind the human alpha 1a receptor has made possible the identification of selective human alpha 1a adrenergic receptor antagonists useful for treating BPH.

Several classes of compounds have been disclosed to be selective alpha 1a adrenergic receptor antagonists useful for treating BPH. WO 94/22829 discloses, for example, certain 4-(un)substituted phenyl-1,4-dihydropyridine derivatives which are described as potent, selective alpha 1a antagonists with weak calcium channel antagonistic activity and which are further described to be anticipated as useful for treating BPH. As another example, WO 96/14846, WO 97/17969 and WO 97/42956 each disclose certain dihydropyrimidine derivatives (e.g., certain 1,2,3,6-tetrahydro-2-oxo-pyrimidine derivatives) which are selective antagonists for the human alpha 1a receptor and useful for treatment of BPH, impotency, cardiac arrhythmia, and other diseases where antagonism of the alpha 1a receptor may be useful. As still another example, WO 96/40135 discloses, inter alia, certain phenylpiperidinyl alkyl saccharin derivatives and their use as selective alpha 1a antagonists. Other examples are U.S. Pat. No. 5,661,163 and WO 96/40136, which disclose, inter alia, piperidinyl- and piperazinyl-alkyl-substituted phenyl acetamides. Yet another example is EP 748800, which discloses, inter alia, certain arylpiperazinyl-propyl substituted pyrimidinediones useful as alpha 1 adrenoceptor antagonists. Still other alpha 1a selective antagonist compounds are disclosed inWO 98/57632, WO 98/57638, WO 98/57639, WO 98/57640, WO 98/57641 and WO 98/57642.

The instant patent disclosure discloses novel dihydro-polyazanaphthalen-2-one compounds which selectively bind to the human alpha 1a receptor. These compounds are further tested for binding to other human alpha 1 receptor subtypes, as well as counterscreened against other types of receptors (e.g., alpha 2), thus defining the specificity of the compounds of the present invention for the human alpha 1a adrenergic receptor.

It is an object of the present invention to identify compounds which bind to the alpha 1a adrenergic receptor. It is a further object of the invention to identify compounds which act as antagonists of the alpha 1a adrenergic receptor. It is another object of the invention to identify alpha 1a adrenergic receptor antagonist compounds which are useful agents for treating BPH in animals, preferably mammals, especially humans. Still another object of the invention is to identify alpha 1a adrenergic receptor antagonists which are useful for relaxing lower urinary tract tissue in animals, preferably mammals, especially humans.

The compounds of the present invention are alpha 1a adrenergic receptor antagonists. Thus, the compounds of the present invention are useful for treating BPH in mammals. Additionally, it has been found that the alpha 1a adrenergic receptor antagonists of the present invention are also useful for relaxing lower urinary tract tissue in mammals.

SUMMARY OF THE INVENTION

The present invention provides dihydro-polyazanaphthalen-2-one compounds and pharmaceutically acceptable salts thereof for the treatment of urinary obstruction caused by benign prostatic hyperplasia (BPH). The compounds antagonize the human alpha 1a adrenergic receptor at nanomolar and subnanomolar concentrations while exhibiting lower affinity for the alpha 1d and alpha 1b human adrenergic receptors and many other G-protein coupled receptors. This invention has the advantage over non-selective alpha 1 adrenoceptor antagonists of reduced side effects related to peripheral adrenergic blockade. Such side effects include hypotension, syncope, lethargy, etc.

More particularly, the present invention is a compound of formula (I):

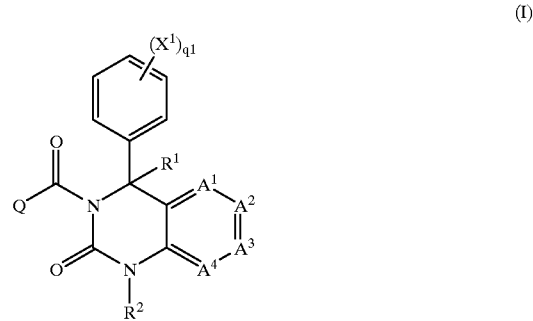

wherein Q is selected from the group consisting of:

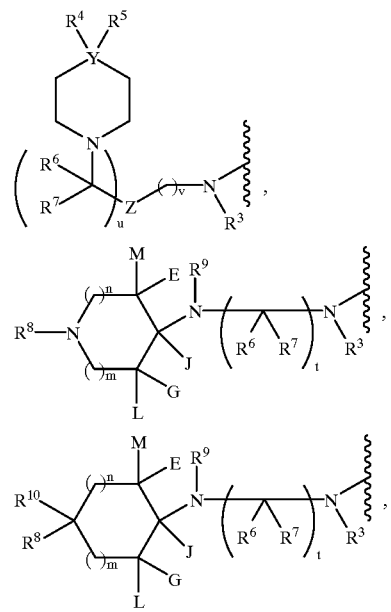

-continued $A^1$, $A^2$, $A^3$ and $A^4$ are each independently selected from C—$X^2$ and N, provided that no more than two of $A^1$, $A^2$, $A^3$ and $A^4$ are N, and further provided that when two of $A^1$, $A^2$, $A^3$ and $A^4$ are N, each nitrogen atom is bonded to two carbon atoms;

each $X^1$ is independently hydrogen, halogen, cyano, nitro, $C_1$–$C_8$ alkyl, $C_3$–$C_8$ cycloalkyl, fluorinated $C_1$–$C_8$ alkyl, fluorinated $C_3$–$C_8$ cycloalkyl, or $(CH_2)_{0-4}OR^a$;

each $X^2$ is independently hydrogen, halogen, cyano, nitro, $C_1$–$C_8$ alkyl, $C_3$–$C_8$ cycloalkyl, fluorinated $C_1$–$C_8$ alkyl, fluorinated $C_3$–$C_8$ cycloalkyl, or $(CH_2)_{0-4}OR^a$;

$R^1$ is hydrogen, $C_1$–$C_8$ alkyl, $C_3$–$C_8$ cycloalkyl, fluorinated $C_1$–$C_8$ alkyl, fluorinated $C_3$–$C_8$ cycloalkyl, phenyl, or substituted phenyl, wherein the substituents on the substituted phenyl are independently selected from halogen, cyano, nitro, $C_1$–$C_8$ alkyl, $C_3$–$C_8$ cycloalkyl, fluorinated $C_1$–$C_8$ alkyl, fluorinated $C_3$–$C_8$ cycloalkyl and $(CH_2)_{0-4}OR^a$;

$R^2$ is hydrogen, $C_{1-8}$ alkyl, or fluorinated $C_1$–$C_8$ alkyl;

$R^3$ is hydrogen, $C_1$–$C_8$ alkyl, or fluorinated $C_1$–$C_8$ alkyl;

Y is carbon or nitrogen, provided that when Y is nitrogen, $R^5$ is absent;

Z is $CH_2$, CHOH, $CHOR^b$, CHF, $CHR^b$, $C(R^b)_2$, $CF_2$, $CHCHF_2$, $C=CF_2$, or C=O;

E, G, L and M are each independently selected from hydrogen, $C_1$–$C_8$ alkyl, fluorinated $C_1$–$C_8$ alkyl, $C_3$–$C_8$ cycloalkyl, fluorinated $C_3$–$C_8$ cycloalkyl, $(CH_2)_{0-4}OR^c$, $(CH_2)_{0-4}N(R^c)_2$, $(CH_2)_{0-4}CN$, $(CH_2)_{0-4}CO_2R^c$, $(CH_2)_{0-4}CON(R^c)_2$, $(CH_2)_{0-4}SO_2R^c$ and $(CH_2)_{0-4}SO_2N(R^c)_2$;

J is hydrogen, $C_1$–$C_8$ alkyl, fluorinated $C_1$–$C_8$ alkyl, $C_3$–$C_8$ cycloalkyl, fluorinated $C_3$–$C_8$ cycloalkyl, $(CH_2)_{1-4}OR^c$, $(CH_2)_{1-4}N(R^c)_2$, $(CH_2)_{1-4}CN$, $(CH_2)_{0-4}CO_2R^c$, $(CH_2)_{0-4}CON(R^c)_2$, $(CH_2)_{0-4}SO_2R^c$, or $(CH_2)_{0-4}SO_2N(R^c)_2$;

$R^4$ is phenyl, substituted phenyl, naphthyl, substituted naphthyl, pyridyl, thienyl, furanyl, substituted pyridyl, substituted thienyl, or substituted furanyl; wherein the substituents on the substituted phenyl are independently selected from halogen, cyano, $OR^c$, $(CH_2)_{0-3}CON(R^c)_2$, $(CH_2)_{0-3}CO_2R^c$, methylenedioxy when the phenyl ring is di-substituted and the substituents are on adjacent carbon atoms, $C_1$–$C_4$ alkyl and fluorinated $C_1$–$C_4$ alkyl; and wherein the substituents on the substituted naphthyl, pyridyl, thienyl, or furanyl are independently selected from phenyl, $OR^c$, halogen, $C_1$–$C_4$ alkyl, fluorinated $C_1$–$C_4$ alkyl, $C_3$–$C_8$ cycloalkyl and fluorinated $C_3$–$C_8$ cycloalkyl;

$R^5$ is hydrogen, cyano, $OR^c$, $CO_2R^c$, $CON(R^c)_2$, tetrazole, isooxadiazole, phenyl, or substituted phenyl; wherein the substituents on the substituted phenyl are independently selected from halogen, cyano, $(CH_2)_{0-3}CON(R^c)_2$, $(CH_2)_{0-3}CO_2R^c$, $OR^c$ methylenedioxy when the phenyl ring is di-substituted and the substituents are on adjacent carbon atoms, $C_1$–$C_4$ alkyl and fluorinated $C_1$–$C_4$ alkyl;

$R^6$ and $R^7$ are each independently selected from hydrogen, $C_1$–$C_8$ alkyl, $C_3$–$C_8$ cycloalkyl, fluorinated $C_1$–$C_8$ alkyl and fluorinated $C_3$–$C_8$ cycloalkyl;

$R^8$ is phenyl, substituted phenyl, naphthyl, substituted naphthyl, pyridyl, substituted pyridyl, pyridyl N-oxide (N→O), substituted pyridyl N-oxide, pyrazinyl, substituted pyrazinyl, thienyl, substituted thienyl, thiazolyl, substituted thiazolyl, furanyl, substituted furanyl, quinazolinyl, or substituted quinazolinyl; wherein the substituents on the phenyl are independently selected from halogen, cyano, nitro, $OR^c$, $N(R^c)_2$, $NR^cCOR^c$, $NR^cCON(R^c)_2$, $NR^cSO_2R^c$, $NR^cSO_2N(R^c)_2$, $(CH_2)_{0-4}CO_2R^c$, $(CH_2)_{0-4}CON(R^c)_2$, $(CH_2)_{0-4}SO_2N(R^c)_2$, $(CH_2)_{0-4}SO_2R^c$, $C_{1-4}$ alkyl and fluorinated $C_1$–$C_4$ alkyl; and wherein the substituents on the substituted naphthyl, pyridyl, pyrazinyl, thienyl, thiazolyl, furanyl, or quinazolinyl are independently selected from cyano, nitro, $N(R^c)_2$, $(CH_2)_{0-4}CO_2R^c$, $(CH_2)_{0-4}CON(R^c)_2$, $(CH_2)_{0-4}SO_2N(R^c)_2$, $(CH_2)_{0-4}SO_2R^c$, phenyl, $OR^c$, halogen, $C_1$–$C_4$ alkyl, fluorinated $C_1$–$C_4$ alkyl, $C_3$–$C_8$ cycloalkyl and fluorinated $C_3$–$C_8$ cycloalkyl;

$R^9$ is hydrogen, $C_1$–$C_8$ alkyl, or fluorinated $C_1$–$C_8$ alkyl;

$R^{10}$ is hydrogen, cyano, $OR^c$, $CO_2R^c$, $CON(R^c)_2$, tetrazole, isooxadiazole, phenyl, substituted phenyl, naphthyl, substituted naphthyl, pyridyl, substituted pyridyl, thienyl, substituted thienyl, furanyl, or substituted furanyl; wherein the substituents on the substituted phenyl are independently selected from halogen, cyano, nitro, $OR^c$, $(CH_2)_{0-4}CO_2R^c$, $(CH_2)_{0-4}CON(R^c)_2$, $N(R^c)_2$, $NR^cCOR^c$, $NR^cCON(R^c)_2$, $NR^cSO_2R^c$, $NR^cSO_2N(R^c)_2$, $(CH_2)_{0-4}SO_2N(R^c)_2$, $(CH_2)_{0-4}SO_2R^c$, $C_1$–$C_4$ alkyl and fluorinated $C_1$–$C_4$ alkyl; and wherein the substituents on the substituted naphthyl, pyridyl, thienyl, or furanyl are independently selected from $(CH_2)_{0-4}CO_2R^c$, $(CH_2)_{0-4}CON(R^c)_2$, $(CH_2)_{0-4}SO_2N(R^c)_2$, $(CH_2)_{0-4}SO_2R^c$, phenyl, $OR^c$, halogen, $C_1$–$C_4$ alkyl, fluorinated $C_1$–$C_4$ alkyl and $C_3$–$C_8$ cycloalkyl;

$R^{13}$, $R^{14}$, $R^{15}$ and $R^{16}$ are each independently selected from hydrogen, $C_1$–$C_8$ alkyl, fluorinated $C_1$–$C_8$ alkyl, $C_3$–$C_8$ cycloalkyl, fluorinated $C_3$–$C_8$ cycloalkyl, and $(CH_2)_{2-4}OR^c$;

$R^{18}$ and $R^{20}$ are each independently selected from hydrogen and $OR^d$;

$R^a$ is hydrogen, $C_1$–$C_8$ alkyl, fluorinated $C_1$–$C_8$ alkyl, or $C_3$–$C_8$ cycloalkyl;

$R^b$ is $C_1$–$C_8$ alkyl, fluorinated $C_1$–$C_8$ alkyl, $C_3$–$C_8$ cycloalkyl, or fluorinated $C_3$–$C_8$ cycloalkyl;

$R^c$ is hydrogen, $C_1$–$C_8$ alkyl, fluorinated $C_1$–$C_8$ alkyl, $C_3$–$C_8$ cycloalkyl, or fluorinated $C_3$–$C_8$ cycloalkyl;

$R^d$ is hydrogen, $C_1$–$C_8$ alkyl, $C_3$–$C_8$ cycloalkyl, or $(CH_2)_{0-4}CF_3$;

m, n, o, and p are each independently integers from 0 to 3;

q1 is an integer from 0 to 5;

t is an integer from 2 to 5;

u and v are each independently integers from 0 to 3; provided that u and v are not both zero; and further provided that when u=0, Z is selected from $CH_2$, CHF, $CHR^b$, $C(R^b)_2$, $CF_2$, $CHCHF_2$ and $C=CF_2$; and w is an integer from 0 to 3, provided that when w is 0, $R^{20}$ is hydrogen;

or a pharmaceutically acceptable salt thereof.

The present invention also includes pharmaceutical compositions, methods of preparing pharmaceutical compositions, and methods of treatment.

These and other embodiments, aspects and features of the present invention are either further described in or will be apparent from the ensuing description, examples and appended claims.

DETAILED DESCRIPTION OF THE INVENTION

The present invention includes dihydro-polyazanaphthalen-2-one compounds of Formula (I) above. These compounds and their pharmaceutically acceptable salts are useful as alpha 1a antagonists.

In a first embodiment, the present invention is a compound of Formula (I), wherein each $X^1$ is independently hydrogen, halogen, cyano, $C_1$–$C_4$ alkyl, $C_3$–$C_6$ cycloalkyl, fluorinated $C_1$–$C_4$ alkyl, fluorinated $C_3$–$C_6$ cycloalkyl, or $(CH_2)_{0-4}OR^a$;

each $X^2$ is independently hydrogen, halogen, cyano, $C_1$–$C_4$ alkyl, $C_3$–$C_6$ cycloalkyl, fluorinated $C_1$–$C_4$ alkyl, fluorinated $C_3$–$C_6$ cycloalkyl, or $(CH_2)_{0-4}OR^a$;

$R^1$ is hydrogen, $C_1$–$C_4$ alkyl, $C_3$–$C_6$ cycloalkyl, fluorinated $C_1$–$C_4$ alkyl, fluorinated $C_3$–$C_6$ cycloalkyl, phenyl, or substituted phenyl, wherein the substituents on the substituted phenyl are independently selected from halogen, cyano, $C_1$–$C_4$ alkyl, fluorinated $C_1$–$C_4$ alkyl and $(CH_2)_{0-4}OR^a$;

$R^2$ is hydrogen or $C_1$–$C_4$ alkyl;

$R^3$ is hydrogen or $C_1$–$C_4$ alkyl;

E, G, L and M are each independently selected from hydrogen and $C_1$–$C_4$ alkyl;

J is hydrogen or $C_1$–$C_4$ alkyl;

$R^4$ is phenyl, mono- or di- or tri-substituted phenyl, pyridyl, thienyl, or furanyl;
wherein the substituents on the substituted phenyl are independently selected from halogen, cyano, $CO_2R^c$, $OR^c$, $CON(R^c)_2$, methylenedioxy, $C_1$–$C_4$ alkyl and fluorinated $C_1$–$C_4$ alkyl;

$R^5$ is hydrogen, cyano, $OR^c$, $CO_2R^c$, $CON(R^c)_2$, phenyl, or mono- or di- or tri-substituted phenyl, wherein the substituents on the substituted phenyl are independently selected from halogen, cyano, $CO_2R^c$, $OR^c$, $CON(R^c)_2$, methylenedioxy, $C_1$–$C_4$ alkyl and fluorinated $C_1$–$C_4$ alkyl;

one of $R^6$ and $R^7$ is hydrogen, and the other of $R^6$ and $R^7$ is hydrogen or $C_1$–$C_4$ alkyl;

$R^8$ is phenyl, mono- or di- or tri-substituted phenyl, pyridyl, or mono- or di- or tri-substituted pyridyl; wherein the substituents on the phenyl are independently selected from halogen, cyano, $OR^c$, $N(R^c)_2$, $NR^cCOR^c$, $NR^cCON(R^c)_2$, $NR^cSO_2R^c$, $NR^cSO_2N(R^c)_2$, $(CH_2)_{0-4}CO_2R^c$, $(CH_2)_{0-4}CON(R^c)_2$, $(CH_2)_{0-4}SO_2N(R^c)_2$, $(CH_2)_{0-4}SO_2R^c$, $C_{1-4}$ alkyl and $CF_3$; and wherein the substituents on the substituted pyridyl are independently selected from cyano, nitro, $N(R^c)_2$, $(CH_2)_{0-4}CO_2R^c$, $(CH_2)_{0-4}CON(R^c)_2$, $(CH_2)_{0-4}SO_2N(R^c)_2$, $(CH_2)_{0-4}SO_2R^c$, phenyl $OR^c$, halogen, $C_1$–$C_4$ alkyl and $CF_3$;

$R^9$ is hydrogen, $C_1$–$C_4$ alkyl, or fluorinated $C_1$–$C_4$ alkyl;

$R^{10}$ is hydrogen, cyano, $OR^c$, $CO_2R^c$, $CON(R^c)_2$, phenyl, or mono- or di- or tri-substituted phenyl wherein the substituents on the phenyl are independently selected from halogen, cyano, $OR^c$, $(CH_2)_{0-4}CO_2R^c$, $(CH_2)_{0-4}CON(R^c)_2$, $N(R^c)_2$, $NR^cCOR^c$, $NR^cCON(R^c)_2$, $NR^cSO_2R^c$, $NR^cSO_2N(R^c)_2$, $(CH_2)_{0-4}SO_2N(R^c)_2$, $(CH_2)_{0-4}SO_2R^c$ and $C_1$–$C_4$ alkyl;

$R^{13}$, $R^{14}$, $R^{15}$ and $R^{16}$ are each independently selected from hydrogen and $C_1$–$C_4$ alkyl;

$R^a$ is hydrogen, $C_1$–$C_4$ alkyl, or $(CH_2)_{0-3}CF_3$;

$R^b$ is $C_1$–$C_4$ alkyl or $(CH_2)_{0-3}CF_3$;

$R^c$ is hydrogen, $C_1$–$C_4$ alkyl, or $(CH_2)_{0-3}CF_3$;

$R^d$ is hydrogen, $C_1$–$C_4$ alkyl, or $(CH_2)_{0-3}CF_3$;

m, n, o, and p are each independently 0 or 1;

q1 is an integer from 0 to 4; and all other variables are as originally defined above;

or a pharmaceutically acceptable salt thereof.

In a second embodiment, the present invention is a compound of Formula (I), wherein each of $A^1$, $A^2$, $A^3$ and $A^4$ is C—$X^2$; and all other variables are as defined in the first embodiment or a pharmaceutically acceptable salt thereof.

In a third embodiment, the present invention is a compound of Formula (I), wherein Q is each of $A^1$, $A^2$, $A^3$ and $A^4$ is C—$X^2$;

each $X^1$ is independently hydrogen, halogen, cyano, $C_1$–$C_4$ alkyl, $C_3$–$C_6$ cycloalkyl, fluorinated $C_1$–$C_4$ alkyl, fluorinated $C_3$–$C_6$ cycloalkyl, or $(CH_2)_{0-4}OR^a$;

each $X^2$ is independently hydrogen, halogen, cyano, $C_1$–$C_4$ alkyl, $C_3$–$C_6$ cycloalkyl, fluorinated $C_1$–$C_4$ alkyl, fluorinated $C_3$–$C_6$ cycloalkyl, or $(CH_2)_{0-4}OR^a$;

$R^1$ is hydrogen, $C_1$–$C_4$ alkyl, $C_3$–$C_6$ cycloalkyl, fluorinated $C_1$–$C_4$ alkyl, fluorinated $C_3$–$C_6$ cycloalkyl, phenyl, or substituted phenyl, wherein the substituents on the substituted phenyl are independently selected from halogen, cyano, $C_1$–$C_4$ alkyl, fluorinated $C_1$–$C_4$ alkyl and $(CH_2)_{0-4}OR^a$;

$R^2$ is hydrogen or $C_1$–$C_4$ alkyl;

$R^3$ is hydrogen or $C_1$–$C_4$ alkyl;

$R^4$ is phenyl, mono- or di- or tri-substituted phenyl, pyridyl, thienyl, or furanyl;
wherein the substituents on the substituted phenyl are independently selected from halogen, cyano, $CO_2R^c$, $OR^c$, $CON(R^c)_2$, methylenedioxy, $C_1$–$C_4$ alkyl and fluorinated $C_1$–$C_4$ alkyl;

$R^5$ is hydrogen, cyano, $OR^c$, $CO_2R^c$, $CON(R^c)_2$, phenyl, or mono- or di- or tri-substituted phenyl, wherein the substituents on the substituted phenyl are independently selected from halogen, cyano, $CO_2R^c$, $OR^c$, $CON(R^c)_2$, methylenedioxy, $C_1$–$C_4$ alkyl and fluorinated $C_1$–$C_4$ alkyl;

one of $R^6$ and $R^7$ is hydrogen, and the other of $R^6$ and $R^7$ is hydrogen or $C_1$–$C_4$ alkyl;

$R^a$ is hydrogen, $C_1$–$C_4$ alkyl, or $(CH_2)_{0-3}CF_3$;

$R^b$ is $C_1$–$C_4$ alkyl or $(CH_2)_{0-3}CF_3$;

$R^c$ is hydrogen, $C_1$–$C_4$ alkyl, or $(CH_2)_{0-3}CF_3$;

q1 is an integer from 0 to 4; and all other variables are as originally defined above;

or a pharmaceutically acceptable salt thereof.

In a first class of the invention is a compound of Formula (II):

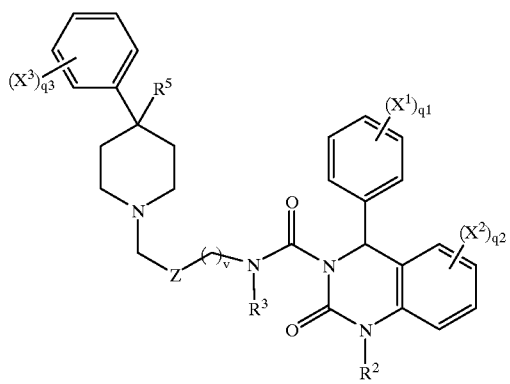

(II)

wherein Z is $CH_2$, CHOH or C=O;

each $X^3$ is independently hydrogen, $CF_3$, cyano, halogen, or $C_1$–$C_4$ alkyl;

$R^5$ is hydrogen, cyano, or $CO_2R^c$;

q2 is an integer from 0 to 4;

q3 is an integer from 0 to 3; and all other variables are as defined in the third embodiment;

or a pharmaceutically acceptable salt thereof.

In a sub-class of the first class is a compound of formula (III):

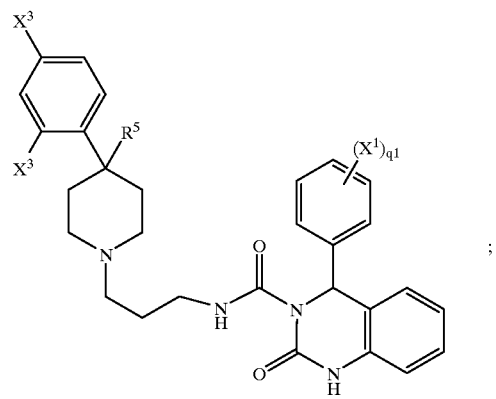

(III)

each $X^1$ is independently hydrogen, fluorine, methyl, ethyl, cyano, $CF_3$, methoxy, ethoxy, or $OCF_3$;

each $X^3$ is independently hydrogen, $CF_3$, cyano, fluorine, methyl, or ethyl;

q1 is an integer from 0 to 2; and all other variables are as defined in the first class;

or a pharmaceutically acceptable salt thereof.

Exemplifying the invention is a compound selected from the group consisting of:

4-(3,4-difluorophenyl)-3-((4-cyano-4-(2-cyanophenyl) piperidin-1-yl)propylcarbamoyl)-3,4-dihydro-quinazolin-2-one;

4-(3,4-difluorophenyl)-3-(-(4-(4-fluorophenyl)piperidin-1-yl)propylcarbamoyl)-3,4-dihydro-quinazolin-2-one;

and pharmaceutically acceptable salts thereof.

In a fourth embodiment, the present invention is a compound of Formula (I), wherein Q is

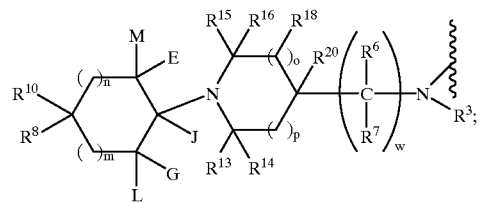

each of $A^1$, $A^2$, $A^3$ and $A^4$ is C—$X^2$;

each $X^1$ is independently hydrogen, halogen, cyano, $C_1$–$C_4$ alkyl, $C_3$–$C_6$ cycloalkyl, fluorinated $C_1$–$C_4$ alkyl, fluorinated $C_3$–$C_6$ cycloalkyl, or $(CH_2)_{0-4}OR^a$;

each $X^2$ is independently hydrogen, halogen, cyano, $C_1$–$C_4$ alkyl, $C_3$–$C_6$ cycloalkyl, fluorinated $C_1$–$C_4$ alkyl, fluorinated $C_3$–$C_6$ cycloalkyl, or $(CH_2)_{0-4}OR^a$;

$R^1$ is hydrogen, $C_1$–$C_4$ alkyl, $C_3$–$C_6$ cycloalkyl, fluorinated $C_1$–$C_4$ alkyl, fluorinated $C_3$–$C_6$ cycloalkyl, phenyl, or substituted phenyl, wherein the substituents on the substituted phenyl are independently selected from halogen, cyano, $C_1$–$C_4$ alkyl, fluorinated $C_1$–$C_4$ alkyl and $(CH_2)_{0-4}OR^a$;

$R^2$ is hydrogen or $C_1$–$C_4$ alkyl;

$R^3$ is hydrogen or $C_1$–$C_4$ alkyl;

E, G, L and M are each independently selected from hydrogen and $C_1$–$C_4$ alkyl;

J is hydrogen or $C_1$–$C_4$ alkyl;

one of $R^6$ and $R^7$ is hydrogen, and the other of $R^6$ and $R^7$ is hydrogen or $C_1$–$C_4$ alkyl;

$R^8$ is selected from phenyl, mono- or di- or tri-substituted phenyl, pyridyl, or mono- or di- or tri-substituted pyridyl; wherein the substituents on the phenyl are independently selected from halogen, cyano, $OR^c$, $N(R^c)_2$, $NR^cCOR^c$, $NR^cCON(R^c)_2$, $NR^cSO_2R^c$, $NR^cSO_2N(R^c)_2$, $(CH_2)_{0-4}CO_2R^c$, $(CH_2)_{0-4}CON(R^c)_2$, $(CH_2)_{0-4}SO_2N(R^c)_2$, $(CH_2)_{0-4}SO_2R^c$, $C_{1-4}$ alkyl and wherein the substituents on the substituted pyridyl are independently selected from cyano, $N(R^c)_2$, $(CH_2)_{0-4}CO_2R^c$, $(CH_2)_{0-4}CON(R^c)_2$, $(CH_2)_{0-4}SO_2N(R^c)_2$, $(CH_2)_{0-4}SO_2R^c$, phenyl, $OR^c$, halogen, $C_1$–$C_4$ alkyl and $CF_3$;

$R^{10}$ is hydrogen, cyano, $OR^c$, $CO_2R^c$, $CON(R^c)_2$, phenyl, or mono- or di- or tri-substituted phenyl, wherein the substituents on the phenyl are independently selected from halogen, cyano, $OR^c$, $(CH_2)_{0-4}CO_2R^c$, $(CH_2)_{0-4}CON(R^c)_2$, $N(R^c)_2$, $NR^cCOR^c$, $NR^cCON(R^c)_2$, $NR^cSO_2R^c$, $NR^cSO_2N(R^c)_2$, $(CH_2)_{0-4}SO_2N(R^c)_2$, $(CH_2)_{0-4}SO_2R^c$ and $C_1$–$C_4$ alkyl;

$R^{13}$, $R^{14}$, $R^{15}$ and $R^{16}$ are each independently selected from hydrogen and $C_1$–$C_4$ alkyl;

$R^a$ is hydrogen, $C_1$–$C_4$ alkyl, or $(CH_2)_{0-3}CF_3$;

$R^c$ is hydrogen, $C_1$–$C_4$ alkyl, or $(CH_2)_{0-3}CF_3$;

$R^d$ is hydrogen, $C_1$–$C_4$ alkyl, or $(CH_2)_{0-4}CF_3$;

m, n, o, and p are each independently 0 or 1;

q1 is an integer from 0 to 4; and all other variables are as originally defined above;

or a pharmaceutically acceptable salt thereof.

In a second class of the invention is a compound of Formula (IV):

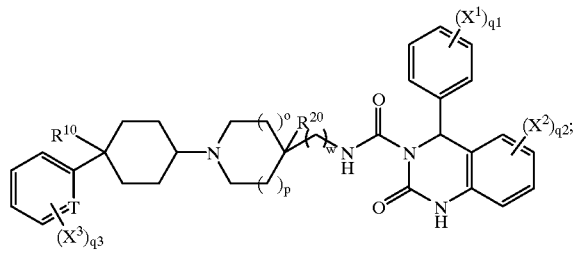

(IV)

wherein T is C—$X^3$ or N;

each $X^3$ is independently hydrogen, halogen, cyano, $OR^c$, $CO_2R^c$, $CON(R^c)_2$, $SO_2N(R^c)_2$, $SO_2R^c$, $C_{1-4}$ alkyl, or $CF_3$;

$R^{10}$ is hydrogen, cyano, or $OR^c$;

$R^{20}$ is hydrogen or OH;

q2 is an integer from 0 to 4;

q3 is an integer from 0 to 3;

w is 0 or 1, provided that when w is 0, $R^{20}$ is hydrogen; and all other variables are as defined in the fourth embodiment;

or a pharmaceutically acceptable salt thereof.

In a sub-class of the second class is a compound of formula (IV), wherein each $X^1$ is fluorine;

each $X^2$ is hydrogen;

$R^{20}$ is hydrogen;

q1 is an integer from 0 to 3;

w is 1; and all other variables are as defined in the second class;

or a pharmaceutically acceptable salt thereof.

Also exemplifying the invention is a compound selected from the group consisting of:

trans-4-(3,4-difluorophenyl)-3-((1-(4-(2-cyanophenyl)cyclohexyl)-3-hydroxy-azetidin-3-yl)methylcarbamoyl)-3,4-dihydro-quinazolin-2-one;

trans-4-(3,4-difluorophenyl)-3-((1-(4-(2-cyanophenyl)cyclohexyl)azetidin-3-yl)methylcarbamoyl)-3,4-dihydro-quinazolin-2-one;

trans-4-(3,4-difluorophenyl)-3-((1-(4-(2-pyridyl)cyclohexyl)azetidin-3-yl)methylcarbamoyl)-3,4-dihydro-quinazolin-2(3H)-one;

and pharmaceutically acceptable salts thereof.

In a third class of the invention is a compound of Formula (V):

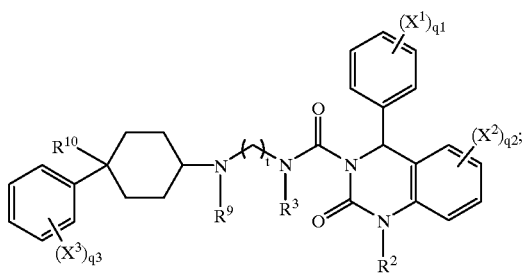

(V)

wherein each $X^1$ is independently hydrogen, halogen, cyano, $C_1$–$C_4$ alkyl, $CF_3$, or $(CH_2)_{0-4}OR^a$; each $X^2$ is independently hydrogen, halogen, cyano, $C_1$–$C_4$ alkyl, $CF_3$, or $(CH_2)_{0-4}OR^a$;

each $X^3$ is independently hydrogen, halogen, cyano, $OR^c$, $CO_2R^c$, $CON(R^c)_2$, $SO_2N(R^c)_2$, $SO_2R^c$, $C_{1-4}$ alkyl, or $CF_3$;

$R^2$ is hydrogen or $C_1$–$C_4$ alkyl;

$R^3$ is hydrogen or $C_1$–$C_4$ alkyl;

$R^9$ is hydrogen or $C_1$–$C_4$ alkyl;

$R^{10}$ is hydrogen, cyano, $OR^c$, $CO_2R^c$, $CON(R^c)_2$, phenyl, or mono- or di- or tri-substituted phenyl, wherein the substituents on the phenyl are independently selected from halogen, cyano, $OR^c$, $(CH_2)_{0-4}CO_2R^c$, $(CH_2)_{0-4}CON(R^c)_2$, $N(R^c)_2$, $NR^cCOR^c$, $NR^cCON(R^c)_2$, $NR^cSO_2R^c$, $NR^cSO_2N(R^c)_2$, $(CH_2)_{0-4}SO_2N(R^c)_2$, $(CH_2)_{0-4}SO_2R^c$, $C_1$–$C_4$ alkyl and fluorinated $C_1$–$C_4$ alkyl;

$R^a$ is hydrogen, $C_1$–$C_4$ alkyl, or $(CH_2)_{0-3}CF_3$;

$R^c$ is hydrogen, $C_1$–$C_4$ alkyl, or $(CH_2)_{0-3}CF_3$;

t is an integer from 2 to 4; and q1, q2 and q3 are each independently integers from 0 to 4;

or a pharmaceutically acceptable salt thereof.

In a sub-class of the third class is a compound of formula (V), wherein each $X^1$ is independently hydrogen, halogen, cyano, methyl, ethyl, $CF_3$, or $OCF_3$;

each $X^2$ is hydrogen;

each $X^3$ is independently hydrogen, halogen, cyano, methyl, ethyl, hydroxy, methoxy, ethoxy, $CO_2R^c$, $CON(R^c)_2$, $SO_2N(R^c)_2$, $SO_2R^c$, $CF_3$, or $OCF_3$;

$R^2$ is hydrogen;
$R^3$ is hydrogen;
$R^9$ is hydrogen;
$R^{10}$ is hydrogen, cyano, or $OR^c$;
$R^c$ is hydrogen, methyl, or ethyl;
t is 2 or 3;
q1 and q3 are each independently integers from 0 to 3; and
all other variables are as defined in the third class;
or a pharmaceutically acceptable salt thereof.

In a fourth class of the invention is a compound of Formula (VI):

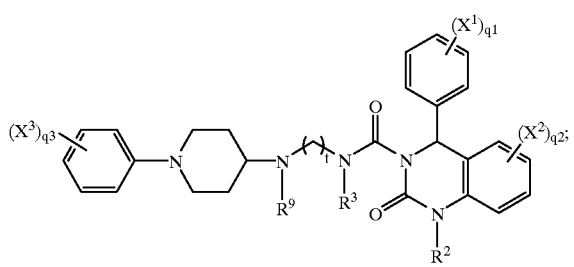

(VI)

wherein each $X^1$ is independently hydrogen, halogen, cyano, $C_1$–$C_4$ alkyl, $CF_3$, or $(CH_2)_{0-4}OR^a$;

each $X^2$ is independently hydrogen, halogen, cyano, $C_1$–$C_4$ alkyl, $CF_3$, or $(CH_2)_{0-4}OR^a$;

each $X^3$ is independently hydrogen, halogen, cyano, $OR^c$, $CO_2R^c$, $CON(R(c))_2$, $SO_2N(R^c)_2$, $SO_2R^c$, $C_{1-4}$ alkyl, or $CF_3$;

$R^2$ is hydrogen or $C_1$–$C_4$ alkyl;

$R^3$ is hydrogen or $C_1$–$C_4$ alkyl;

$R^9$ is hydrogen or $C_1$–$C_4$ alkyl;

$R^a$ is hydrogen, $C_1$–$C_4$ alkyl, or $(CH_2)_{0-3}CF_3$;

$R^c$ is hydrogen, $C_1$–$C_4$ alkyl, or $(CH_2)_{0-3}CF_3$;

t is an integer from 2 to 4; and q1, q2 and q3 are each independently integers from 0 to 4;

or a pharmaceutically acceptable salt thereof.

In a sub-class of the fourth class is a compound of formula (VI), wherein each $X^1$ is independently hydrogen, halogen, cyano, methyl, ethyl, $CF_3$, or $OCF_3$;

each $X^2$ is hydrogen;

each $X^3$ is independently hydrogen, halogen, cyano, methyl, ethyl, hydroxy, methoxy, ethoxy, $CO_2R^c$, $CON(R^c)_2$, $SO_2N(R^c)_2$, $SO_2R^c$, $CF_3$, or $OCF_3$;

$R^2$ is hydrogen;

$R^3$ is hydrogen;

$R^9$ is hydrogen;

$R^c$ is hydrogen, methyl, or ethyl;

t is 2 or 3;

q1 and q3 are each independently integers from 0 to 3; and all other variables are as defined in the fourth class;

or a pharmaceutically acceptable salt thereof.

In a fifth class of the invention is a compound of Formula (VII):

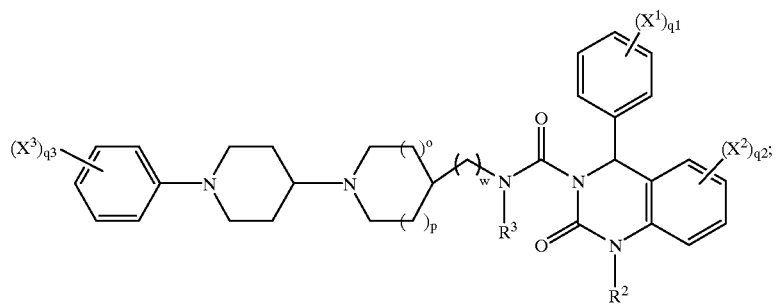

(VII)

wherein each $X^1$ is independently hydrogen, halogen, cyano, $C_1$–$C_4$ alkyl, $CF_3$, or $(CH_2)_{0-4}OR^a$;

each $X^2$ is independently hydrogen, halogen, cyano, $C_1$–$C_4$ alkyl, $CF_3$, or $(CH_2)_{0-4}OR^a$;

each $X^3$ is independently hydrogen, halogen, cyano, $OR^c$, $CO_2R^c$, $CON(R^c)_2$, $SO_2N(R^c)_2$, $SO_2R^c$, $C_{1-4}$ alkyl, or $CF_3$;

$R^2$ is hydrogen or $C_1$–$C_4$ alkyl;

$R^3$ is hydrogen or $C_1$–$C_4$ alkyl;

$R^a$ is hydrogen, $C_1$–$C_4$ alkyl, or $(CH_2)_{0-3}CF_3$;

$R^c$ is hydrogen, $C_1$–$C_4$ alkyl, or $(CH_2)_{0-3}CF_3$;

o and p are each independently 0 or 1;

w is an integer from 0 to 2; and q1, q2 and q3 are each independently integers from 0 to 4;

or a pharmaceutically acceptable salt thereof.

In a sub-class of the fifth class is a compound of formula (VII), wherein each $X^1$ is independently hydrogen, halogen, cyano, methyl, ethyl, $CF_3$, or $OCF_3$;

each $X^2$ is hydrogen;
each $X^3$ is independently hydrogen, halogen, cyano, methyl, ethyl, hydroxy, methoxy, ethoxy, $CO_2R^c$, $CON(R^c)_2$, $SO_2N(R^c)_2$, $SO_2R^c$, $CF_3$, or $OCF_3$;
$R^2$ is hydrogen;
$R^3$ is hydrogen;
$R^c$ is hydrogen, methyl, or ethyl;
w is 0 or 1;
q1 and q3 are each independently integers from 0 to 3; and all other variables are as defined in the fifth class;
or a pharmaceutically acceptable salt thereof.

In a sixth class of the invention is a compound of Formula (VIII):

(VIII)

wherein
each $X^1$ is independently hydrogen, halogen, cyano, $C_1$–$C_4$ alkyl, $CF_3$, or $(CH_2)_{0-4}OR^a$;
each $X^2$ is independently hydrogen, halogen, cyano, $C_1$–$C_4$ alkyl, $CF_3$, or $(CH_2)_{0-4}OR^a$;
each $X^3$ is independently hydrogen, halogen, cyano, $OR^c$, $CO_2R^c$, $CON(R^c)_2$, $SO_2N(R^c)_2$, $SO_2R^c$, $C_{1-4}$ alkyl, or $CF_3$;
$R^2$ is hydrogen or $C_1$–$C_4$ alkyl;
$R^9$ is hydrogen or $C_1$–$C_4$ alkyl;
$R^{10}$ is hydrogen, cyano, $OR^c$, $CO_2R^c$, $CON(R^c)_2$, phenyl, or mono- or di- or tri-substituted phenyl, wherein the substituents on the phenyl are independently selected from halogen, cyano, $OR^c$, $(CH_2)_{0-4}CO_2R^c$, $(CH_2)_{0-4}CON(R^c)_2$, $N(R^c)_2$, $NR^cCOR^c$, $NR^cCON(R^c)_2$, $NR^cSO_2R^c$, $NR^cSO_2N(R^c)_2$, $(CH_2)_{0-4}SO_2N(R^c)_2$, $(CH_2)_{0-4}SO_2R^c$, $C_1$–$C_4$ alkyl and fluorinated $C_1$–$C_4$ alkyl;
$R^a$ is hydrogen, $C_1$–$C_4$ alkyl, or $(CH_2)_{0-3}CF_3$;
$R^c$ is hydrogen, $C_1$–$C_4$ alkyl, or $(CH_2)_{0-3}CF_3$;
o and p are each independently 0 or 1;
w is an integer from 0 to 2;
q1, q2 and q3 are each independently integers from 0 to 4;
or a pharmaceutically acceptable salt thereof.

In a sub-class of the sixth class is a compound of formula (VIII), wherein
each $X^1$ is independently hydrogen, halogen, cyano, methyl, ethyl, $CF_3$, or $OCF_3$;
each $X^2$ is hydrogen;
each $X^3$ is independently hydrogen, halogen, cyano, methyl, ethyl, hydroxy, methoxy, ethoxy, $CO_2R^c$, $CON(R^c)_2$, $SO_2N(R^c)_2$, $SO_2R^c$, $CF_3$, or $OCF_3$;
$R^2$ is hydrogen;
$R^9$ is hydrogen;
$R^{10}$ is hydrogen, cyano, or $OR^c$;
$R^c$ is hydrogen, methyl, or ethyl;
w is 0 or 1;
q1 and q3 are each independently integers from 0 to 3; and all other variables are as defined in the sixth class;
or a pharmaceutically acceptable salt thereof.

In a seventh class of the invention is a compound of Formula (IX):

(IX)

wherein
each $X^1$ is independently hydrogen, halogen, cyano, $C_1$–$C_4$ alkyl, $CF_3$, or $(CH_2)_{0-4}OR^a$;
each $X^2$ is independently hydrogen, halogen, cyano, $C_1$–$C_4$ alkyl, $CF_3$, or $(CH_2)_{0-4}OR^a$;
each $X^3$ is independently hydrogen, halogen, cyano, $OR^c$, $CO_2R^c$, $CON(R^c)_2$, $SO_2N(R^c)_2$, $SO_2R^c$, $C_{1-4}$ alkyl, or $CF_3$;
$R^2$ is hydrogen or $C_1$–$C_4$ alkyl;
$R^9$ is hydrogen or $C_1$–$C_4$ alkyl;
$R^a$ is hydrogen, $C_1$–$C_4$ alkyl, or $(CH_2)_{0-3}CF_3$;
$R^c$ is hydrogen, $C_1$–$C_4$ alkyl, or $(CH_2)_{0-3}CF_3$;
o and p are each independently 0 or 1;
w is an integer from 0 to 2; and
q1, q2 and q3 are each independently integers from 0 to 4;
or a pharmaceutically acceptable salt thereof.

In a sub-class of the seventh class is a compound of formula (IX), wherein
each $X^1$ is independently hydrogen, halogen, cyano, methyl, ethyl, $CF_3$, or $OCF_3$;
each $X^2$ is hydrogen;
each $X^3$ is independently hydrogen, halogen, cyano, methyl, ethyl, hydroxy, methoxy, ethoxy, $CO_2R^c$, $CON(R^c)_2$, $SO_2N(R^c)_2$, $SO_2R^c$, $CF_3$, or $OCF_3$;
$R^2$ is hydrogen;
$R^9$ is hydrogen;
$R^c$ is hydrogen, methyl, or ethyl;
w is 0 or 1;
q1 and q3 are each independently integers from 0 to 3; and all other variables are as defined in the seventh class;
or a pharmaceutically acceptable salt thereof.

The present invention also includes a pharmaceutical composition comprising a therapeutically effective amount of any of the compounds described above and a pharmaceutically acceptable carrier. In one embodiment is a pharmaceutical composition made by combining any of the compounds described above and a pharmaceutically acceptable carrier. The present invention further includes a process for making a pharmaceutical composition comprising combining any of the compounds described above and a pharmaceutically acceptable carrier.

The present invention further includes a pharmaceutical composition as described in the preceding paragraph further comprising a therapeutically effective amount of a testosterone 5-alpha reductase inhibitor. In one embodiment, the testosterone 5-alpha reductase inhibitor is a type 1, a type 2, both a type 1 and a type 2 (i.e., a three component combination comprising any of the compounds described above combined with both a type 1 testosterone 5-alpha reductase inhibitor and a type 2 testosterone 5-alpha reductase inhibitor), or a dual type 1 and type 2 testosterone 5-alpha reductase inhibitor. In another embodiment, the testosterone 5-alpha reductase inhibitor is a type 2 testosterone 5-alpha reductase inhibitor. The testosterone 5-alpha reductase inhibitor is suitably finasteride.

The present invention also includes a method of treating benign prostatic hyperplasia in a subject in need thereof which comprises administering to the subject a therapeutically effective amount of any of the compounds (or any of the compositions) described above. In one embodiment of the method of treating BPH, the compound (or composition) does not cause a fall in blood pressure at dosages effective to alleviate BPH. In another embodiment of the method of treating BPH, the compound is administered in combination with a testosterone 5-alpha reductase inhibitor. A suitable testosterone 5-alpha reductase inhibitor for use in the method is finasteride.

The present invention also includes a method of inhibiting contraction of prostate tissue or relaxing lower urinary tract tissue in a subject in need thereof which comprises administering to the subject a therapeutically effective amount of any of the compounds (or any of the compositions) described above. In one embodiment of the method of inhibiting contraction of prostate tissue or relaxing lower urinary tract tissue, the compound (or composition) additionally does not cause a fall in blood pressure at dosages effective to inhibit contraction of prostate tissue. In another embodiment, the compound is administered in combination with a testosterone 5-alpha reductase inhibitor; the testosterone 5-alpha reductase inhibitor is suitably finasteride.

The present invention also includes a method of treating a disease which is susceptible to treatment by antagonism of the alpha 1a receptor which comprises administering to a subject in need thereof an amount of any of the compounds described above effective to treat the disease. Diseases which are susceptible to treatment by antagonism of the alpha 1a receptor include, but are not limited to, BPH, high intraocular pressure, high cholesterol, impotency, sympathetically mediated pain, migraine (see Vatz, *Headache* (1997), 37: 107–108) and cardiac arrhythmia.

The present invention also includes the use of any of the compounds described above in the preparation of a medicament for: a) treating benign prostatic hyperplasia; b) relaxing lower urinary tract tissue; or c) inhibiting contraction of prostate tissue; in a subject in need thereof.

The present invention further includes the use of any of the alpha 1a antagonist compounds described above and a 5-alpha reductase inhibitor for the manufacture of a medicament for: a) treating benign prostatic hyperplasia; b) relaxing lower urinary tract tissue; or c) inhibiting contraction of prostate tissue which comprises an effective amount of the alpha 1a antagonist compound and an effective amount of 5-alpha reductase inhibitor, together or separately.

As used herein, the term "$C_1$–$C_8$ alkyl" means linear or branched chain alkyl groups having from 1 to 8 carbon atoms and includes all of the octyl alkyl, heptyl alkyl, hexyl alkyl and pentyl alkyl isomers as well as n-, iso-, sec- and t-butyl, n- and isopropyl, ethyl and methyl. "$C_1$–$C_4$ alkyl" means n-, iso-, sec- and t-butyl, n- and isopropyl, ethyl and methyl.

The term "$C_1$–$C_6$ alkoxy" means an —O-alkyl group wherein alkyl is $C_1$ to $C_6$ alkyl. "$C_1$–$C_4$ alkoxy" has an analogous meaning; i.e., it is an alkoxy group selected from methoxy, ethoxy, n-propoxy, isopropoxy, n-butoxy, isobutoxy, tert-butoxy, and sec-butoxy.

The term "$C_3$–$C_8$ cycloalkyl" means a cyclic ring of an alkane having three to eight total carbon atoms (i.e., cyclopropyl, cyclobutyl, cyclopentyl, cyclohexyl, cycloheptyl or cyclooctyl). "$C_3$–$C_6$ cycloalkyl" refers to a cyclic ring selected from cyclopropyl, cyclobutyl, cyclopentyl, and cyclohexyl.

The term "$C_1$–$C_8$ alkyl-$C_3$–$C_8$ cycloalkyl" means a $C_3$–$C_8$ cycloalkyl group as defined above substituted with one or more linear or branched chain alkyl groups having from 1 to 8 carbon atoms.

The term "$C_3$–$C_8$ cycloalkyl-$C_1$–$C_8$ alkyl" means a $C_1$–$C_8$ alkyl group as defined above substituted with one or more cyclic alkyl groups having from 3 to 8 carbon atoms.

The term "halogen" (which may alternatively be referred to as "halo") refers to fluorine, chlorine, bromine and iodine (alternatively, fluoro, chloro, bromo, and iodo).

The term "fluorinated $C_1$–$C_8$ alkyl" (which may alternatively be preferred to as "$C_1$–$C_8$ fluoroalkyl") means a $C_1$ to $C_8$ linear or branched alkyl group as defined above with one or more fluorine substituents. The term "fluorinated $C_1$–$C_4$ alkyl" has an analogous meaning. Representative examples of suitable fluoroalkyls include the series $(CH_2)_{0-4}CF_3$ (i.e., trifluoromethyl, 2,2,2-trifluoroethyl, 3,3,3-trifluoro-n-propyl, etc.), 1-fluoroethyl, 2-fluoroethyl, 2,2-difluoroethyl, 3,3,3-trifluoroisopropyl, 1,1,1,3,3,3-hexafluoroisopropyl, and perfluorohexyl.

The term "fluorinated $C_3$–$C_8$ cycloalkyl" (which may alternatively be referred to as "$C_3$–$C_8$ fluorocycloalkyl") means a cycloalkyl group as defined above with one or more fluorine substituents. "Fluorinated $C_3$–$C_6$ cycloalkyl" has an analogous meaning. Representative examples of suitable fluorocycloalkyls include all isomers of fluorocyclohexyl (i.e., 1-, 2-, 3-, and 4-fluorocyclohexyl), difluorocyclohexyl (e.g., 2,4-difluorocyclohexyl, 3,4-difluorocyclohexyl, etc.), fluorocyclopentyl, and so forth.

The term "fluorinated $C_1$–$C_6$ alkoxy" (which may alternatively be referred to as "$C_1$–$C_6$ fluoroalkoxy") means a $C_1$–$C_6$ alkoxy group as defined above wherein the alkyl moiety has one or more fluorine substituents. "Fluorinated $C_1$–$C_4$ alkoxy" has an analogous meaning. Representative examples include the series $O(CH_2)_{0-4}CF_3$ (i.e., trifluoromethoxy, 2,2,2-trifluoroethoxy, 3,3,3-trifluoro-n-propoxy, etc.), 1,1,1,3,3,3-hexafluoroisopropoxy, and so forth.

The term "heterocyclic" (which may alternatively be referred to as "heterocycle") refers to a stable 5- to 7-membered monocyclic ring system which may be saturated or unsaturated; which consists of carbon atoms and from one to three heteroatoms selected from N, O or S, and wherein the nitrogen and sulfur heteroatoms may optionally be oxidized, and the nitrogen heteroatom may optionally be quaternized; and which is optionally substituted with one or more substituent groups including, but not limited to, halo, cyano, alkyl, fluoroalkyl, alkoxy, fluoroalkoxy, alkylalkoxy, cycloalkyl, fluorocycloalkyl, amino, aryl (e.g., phenyl), carboxy, carboxylate, sulfonamido, sulfonyl, and the like. Suitable heterocyclic groups include, but are not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl. Morpholino is the same as morpholinyl.

The term "thienyl," as used herein, refers to the group

The term "aryl" refers herein to aromatic mono- and poly-carbocyclic ring systems, optionally substituted, including, but not limited to, phenyl, substituted phenyl, naphthyl, and substituted naphthyl.

The term "heteroaryl" refers to aromatic heterocyclic or substituted aromatic heterocyclic ring systems, including, but not limited to, pyridyl, substituted pyridyl, pyridyl N-oxide (N(7)O), substituted pyridyl N-oxide, pyrazinyl, substituted pyrazinyl, thienyl, substituted thienyl, thiazolyl, substituted thiazolyl, furanyl, substituted furanyl, quinazolinyl, and substituted quinazolinyl.

The term "substituted" includes mono- and poly-substitution by a named substituent to the extent such single and multiple substitution is chemically allowed.

It is understood that the definition of a substituent (e.g., $CO_2R^c$) or variable (e.g., $R^c$) at a particular location in a molecule is independent of its definitions at other locations in that molecule. Thus, for example, when $R^4$ is mono-substituted phenyl wherein the substituent is $CO_2R^c=CO_2H$, and $R^5$ is also mono-substituted phenyl wherein the substituent is $CO_2R^c$, it is understood that the substituent on the phenyl in $R^5$ can be any one of $CO_2H$, $CO_2Me$, $CO_2Et$, $CO_2Pr$, $CH_2CO_2H$, $CH_2CO_2Me$, $CH_2CO_2Et$, $CH_2CO_2Pr$, $(CH_2)_2CO_2H$, etc. As another example, $NR^cC(=O)R^c$ represents $NHC(=O)H$, $NHC(=O)Me$, $NMeC(=O)Me$, $NMeC(=O)Et$, etc.

It is also understood that the definition of a substituent or variable at a particular location in a molecule is independent of the definition of another occurrence of the same substituent or variable at the same location. Thus, $C(=O)N(R^c)_2$ represents groups such as $-C(=O)NH_2$, $-C(=O)NHCH_3$, $-C(=O)NHC_2H_5$, $-C(=O)N(CH_3)C_2H_5$, etc.

It is understood that substituents and substitution patterns on the compounds of the instant invention can be selected by one of ordinary skill in the art to provide compounds that are chemically stable and that can be readily synthesized by the methods set forth below and, when viewed in the light of this disclosure, by techniques known in the art. Where multiple substituent moieties are disclosed or claimed, the substituted compound can be independently substituted by one or more of the disclosed or claimed substituent moieties, singly or plurally. Representative embodiments for the variables and substituents set forth in Formula (I) include the following:

$A^1$, $A^2$, $A^3$ and $A^4$ are each independently selected from $C-X^2$ or N, provided that no more than two of $A^1$, $A^2$, $A^3$ and $A^4$ are nitrogen, and further provided that when two of $A^1$, $A^2$, $A^3$ and $A^4$ are N, each nitrogen atom is bonded to two carbon atoms. In one embodiment, $A^1$ and $A^4$ are nitrogen and $A^2$ and $A^3$ are $C-X^2$. In another embodiment, $A^2$ and $A^4$ are nitrogen and $A^1$ and $A^3$ are $C-X^2$. In yet another embodiment, one of $A^1$, $A^2$, $A^3$ and $A^4$ is nitrogen, and the others are $C-X^2$. In still another embodiment, all of $A^1$, $A^2$, $A^3$ and $A^4$ are $C-X^2$.

Each $X^1$ is independently hydrogen, halogen, cyano, nitro, $C_1-C_8$ alkyl, $C_3-C_8$ cycloalkyl, fluorinated $C_1-C_8$ alkyl, fluorinated $C_3-C_8$ cycloalkyl, or $(CH_2)_{0-4}OR^a$; or is independently hydrogen, halogen, cyano, $C_1-C_4$ alkyl, fluorinated $C_1-C_4$ alkyl, $C_3-C_6$ cycloalkyl, fluorinated $C_3-C_6$ cycloalkyl, or $(CH_2)_{0-4}OR^a$; or is independently hydrogen, halogen, cyano, $C_1-C_4$ alkyl, $(CH_2)_{0-4}CF_3$, or $(CH_2)_{0-4}CF_3$; or is independently hydrogen, halogen, cyano, $C_1-C_4$ alkyl, $CF_3$, or $(CH_2)_{0-4}OR^a$. In another embodiment, each $X^1$ is independently hydrogen, halogen, cyano, methyl, ethyl, $CF_3$, or $OCF_3$. In another embodiment, each $X^1$ is independently hydrogen, fluorine, cyano, methyl, ethyl, $CF_3$, or $OCF_3$. In still another embodiment, each $X^1$ is fluorine.

Each $X^2$ is independently hydrogen, halogen, cyano, nitro, $C_1-C_8$ alkyl, $C_3-C_8$ cycloalkyl, fluorinated $C_1-C_8$ alkyl, fluorinated $C_3-C_8$ cycloalkyl, or $(CH_2)_{0-4}OR^a$; or is independently hydrogen, halogen, cyano, $C_1-C_4$ alkyl, fluorinated $C_1-C_4$ alkyl, $C_3-C_6$ cycloalkyl, fluorinated $C_3-C_6$ cycloalkyl, or $(CH_2)_{0-4}OR^a$; or is independently hydrogen, halogen, cyano, $C_1-C_4$ alkyl, $(CH_2)_{0-4}CF_3$, or $(CH_2)_{0-4}CF_3$; or is independently hydrogen, halogen, cyano, $C_1-C_4$ alkyl, $CF_3$, or $(CH_2)_{0-4}OR^a$. In another embodiment, each $X^2$ is independently hydrogen, halogen, cyano, methyl, ethyl, $CF_3$, or $OCF_3$. In still another embodiment, each $X^2$ is hydrogen.

One aspect of the embodiment in which all of $A^1$, $A^2$, $A^3$ and $A^4$ are $C-X^2$ is the dihydroquinazolin-2-one moiety of formula:

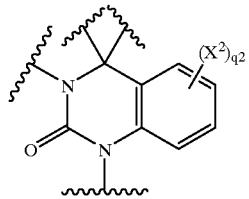

wherein $X^2$ is as defined above; and q2 is an integer from 0 to 4; or from 0 to 3; or from 0 to 2; or is 0 or 1; or is 0; or is 1.

$R^1$ is hydrogen, $C_1-C_8$ alkyl, $C_3-C_8$ cycloalkyl, fluorinated $C_1-C_8$ alkyl, fluorinated $C_3-C_8$ cycloalkyl, phenyl, or substituted phenyl; or is hydrogen, $C_1-C_4$ alkyl, $C_3-C_6$ cycloalkyl, fluorinated $C_1-C_4$ alkyl, fluorinated $C_3-C_6$ cycloalkyl, phenyl, or substituted phenyl; or is hydrogen, $C_1-C_4$ alkyl, $C_3-C_6$ cycloalkyl, fluorinated $C_1-C_4$ alkyl, fluorinated $C_3-C_6$ cycloalkyl, phenyl, or mono- or di- or tri-substituted phenyl. In another embodiment, $R^1$ is hydrogen.

In $R^1$, the substituents on the substituted phenyl are independently selected from halogen, cyano, nitro, $C_1-C_8$ alkyl, $C_3-C_8$ cycloalkyl, fluorinated $C_1-C_8$ alkyl, fluorinated $C_3-C_8$ cycloalkyl and $(CH_2)_{0-4}OR^a$; or are independently selected from halogen, cyano, $C_1-C_4$ alkyl, $C_3-C_6$ cycloalkyl, fluorinated $C_1-C_4$ alkyl, fluorinated $C_3-C_6$ cycloalkyl and $(CH_2)_{0-4}OR^a$.

$R^2$ is hydrogen, $C_1-C_8$ alkyl, or fluorinated $C_1-C_8$ alkyl; or is hydrogen, $C_1-C_4$ alkyl, or fluorinated $C_1-C_4$ alkyl; or is hydrogen or $C_1-C_4$ alkyl. In another embodiment, $R^2$ is hydrogen.

$R^3$ is hydrogen, $C_1-C_8$ alkyl, or fluorinated $C_1-C_8$ alkyl; or is hydrogen, $C_1-C_4$ alkyl, or fluorinated $C_1-C_4$ alkyl; or is hydrogen or $C_1-C_4$ alkyl. In another embodiment, $R^3$ is hydrogen.

Y is carbon or nitrogen, provided that when Y is nitrogen, $R^5$ is absent. In one embodiment, Y is carbon.

Z is $CH_2$, $CHOR^b$, CHF, $CHR^b$, $C(R^b)_2$, $CF_2$, $CHCHF_2$, $C=CF_2$, or C=O. In one embodiment, Z is $CH_2$, CHF, $CHR^b$, $C(R^b)_2$, $CF_2$, $CHCHF_2$, or $C=CF_2$. In another embodiment, Z is $CH_2$, CHOH, or C=O, provided that when u is zero, Z is $CH_2$.

E, G, L and M are each independently selected from hydrogen, $C_1$–$C_8$ alkyl, fluorinated $C_1$–$C_8$ alkyl, $C_3$–$C_8$ cycloalkyl, fluorinated $C_3$–$C_8$ cycloalkyl, $(CH_2)_{0-4}OR^c$, $(CH_2)_{0-4}N(R^c)_2$, $(CH_2)_{0-4}CN$, $(CH_2)_{0-4}CO_2R^c$, $(CH_2)_{0-4}CON(R^c)_2$, $(CH_2)_{0-4}SO_2R^c$ and $(CH_2)_{0-4}SO_2N(R^c)_2$; or are each independently selected from hydrogen, $C_1$–$C_4$ alkyl and fluorinated $C_1$–$C_4$ alkyl; or are each independently selected from hydrogen, $C_1$–$C_4$ alkyl and $(CH_2)_{0-3}CF_3$; or are each independently selected from hydrogen and $C_1$–$C_4$ alkyl. In one embodiment, E, G, L and M are all hydrogen.

J is hydrogen, $C_1$–$C_8$ alkyl, fluorinated $C_1$–$C_8$ alkyl, $C_3$–$C_8$ cycloalkyl, fluorinated $C_3$–$C_8$ cycloalkyl, $(CH_2)_{1-4}OR^c$, $(CH_2)_{1-4}N(R^c)_2$, $(CH_2)_{1-4}CN$, $(CH_2)_{0-4}CO_2R^c$, $(CH_2)_{0-4}CON(R^c)_2$, $(CH_2)_{0-4}SO_2R^c$, or $(CH_2)_{0-4}SO_2N(R^c)_2$; or is hydrogen, $C_1$–$C_4$ alkyl or fluorinated $C_1$–$C_4$ alkyl; or is hydrogen, $C_1$–$C_4$ alkyl, or $(CH_2)_{0-3}CF_3$; or is hydrogen or $C_1$–$C_4$ alkyl; or is hydrogen.

$R^4$ is phenyl, substituted phenyl, naphthyl, substituted naphthyl, pyridyl, thienyl, furanyl, substituted pyridyl, substituted thienyl, or substituted furanyl; or is phenyl, mono- or di- or tri-substituted phenyl, pyridyl, thienyl, or furanyl; or is phenyl or mono- or di- or tri-substituted phenyl; or is phenyl or mono-substituted phenyl.

In $R^4$, the substituents on the substituted phenyl are independently selected from halogen, cyano, $OR^c$, $(CH_2)_{0-3}CON(R^c)_2$, $(CH_2)_{0-3}CO_2R^c$, methylenedioxy when the phenyl ring is di-substituted and the substituents are on adjacent carbon atoms, $C_1$–$C_4$ alkyl and fluorinated $C_1$–$C_4$ alkyl; or are independently selected from halogen, cyano, $CO_2R^c$, $OR^c$, $CON(R^c)_2$, methylenedioxy, $C_1$–$C_4$ alkyl and fluorinated $C_1$–$C_4$ alkyl; or are independently selected from $CF_3$, cyano, halogen (e.g., fluorine), and $C_1$–$C_4$ alkyl.

In $R^4$, the substituents on the substituted naphthyl, pyridyl, thienyl, or furanyl are independently selected from phenyl, $OR^c$, halogen, $C_1$–$C_4$ alkyl, fluorinated $C_1$–$C_4$ alkyl, $C_3$–$C_8$ cycloalkyl and fluorinated $C_3$–$C_8$ cycloalkyl; or are independently selected from $CF_3$, phenyl, $OR^c$, halogen, and $C_1$–$C_4$ alkyl.

In one embodiment, $R^4$ is represented by the formula:

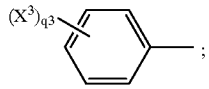

wherein each $X^3$ is independently halogen, cyano, $OR^c$, $(CH_2)_{0-3}CON(R^c)_2$, $(CH_2)_{0-3}CO_2R^c$, $C_1$–$C_4$ alkyl or fluorinated $C_1$–$C_4$ alkyl; and q3 is an integer of from 0 to 5; or from 0 to 4; or from 0 to 3; or from 0 to 2; or is 0 or 1. In other embodiments, each $X^3$ is independently hydrogen, halogen, cyano, $OR^c$, $CO_2R^c$, $CON(R^c)_2$, $SO_2N(R^c)_2$, $SO_2R^c$, $C_1$–$C_4$ alkyl, or $CF_3$; or is independently hydrogen, $CF_3$, cyano, halogen, or $C_1$–$C_4$ alkyl; or is independently hydrogen, $CF_3$, cyano, fluorine, methyl, or ethyl; or is independently hydrogen, $CF_3$, cyano, or fluorine.

$R^5$ is hydrogen, cyano, $OR^c$, $CO_2R^c$, $CON(R^c)_2$, tetrazole, isooxadiazole, phenyl, or substituted phenyl; or is hydrogen, cyano, $OR^c$, $CO_2R^c$, $CON(R^c)_2$, phenyl, or mono- or di- or tri-substituted phenyl; or is hydrogen, cyano, $CO_2R^c$, CON$(R^c)_2$, tetrazole and isooxadiazole; or is hydrogen, cyano, or $CO_2R^c$; or is cyano or $CO_2R^c$. In one embodiment, $R^5$ is cyano or $CO_2CH_3$.

In $R^5$, the substituents on the substituted phenyl are independently selected from halogen, cyano, $(CH_2)_{0-3}CON(R^c)_2$, $(CH_2)_{0-3}CO_2R^c$, methylenedioxy when the phenyl ring is di-substituted and the substituents are on adjacent carbon atoms, $C_1$–$C_4$ alkyl and fluorinated $C_1$–$C_4$ alkyl; or are independently selected from halogen, cyano, $CO_2R^c$, $OR^c$, $CON(R^c)_2$, methylenedioxy, $C_1$–$C_4$ alkyl and fluorinated $C_1$–$C_4$ alkyl.

$R^6$ and $R^7$ are each independently selected from hydrogen, $C_1$–$C_8$ alkyl, $C_3$–$C_8$ cycloalkyl, fluorinated $C_1$–$C_8$ alkyl and fluorinated $C_3$–$C_8$ cycloalkyl; or one of $R^6$ and $R^7$ is hydrogen, and the other of $R^6$ and $R^7$ is hydrogen or $C_1$–$C_4$ alkyl. In another embodiment, $R^6$ and $R^7$ are both hydrogen. In still another embodiment, $R^6$ and $R^7$ together with the carbon atom to which they are attached form methylene (—$CH_2$—) units or alkylidene units of formula (—CR'H—) wherein R' is $C_1$–$C_4$ alkyl or, in cases where there are at least two $CR^6R^7$'s (e.g., when w=2), mixtures of the foregoing units.

$R^8$ is phenyl, substituted phenyl, naphthyl, substituted naphthyl, pyridyl, substituted pyridyl, pyridyl N-oxide (N(7)O), substituted pyridyl N-oxide, pyrazinyl, substituted pyrazinyl, thienyl, substituted thienyl, thiazolyl, substituted thiazolyl, furanyl, substituted furanyl, quinazolinyl, or substituted quinazolinyl; or is phenyl, mono- or di- or tri-substituted phenyl, pyridyl, or mono- or di- or tri-substituted pyridyl; or is phenyl or mono- or di- or tri-substituted phenyl.

In $R^8$, the substituents on the phenyl are independently selected from halogen, cyano, nitro, $OR^c$, $N(R^c)_2$, $NR^cCOR^c$, $NR^cCON(R^c)_2$, $NR^cSO_2R^c$, $NR^cSO_2N(R^c)_2$, $(CH_2)_{0-4}CO_2R^c$, $(CH_2)_{0-4}CON(R^c)_2$, $(CH_2)_{0-4}SO_2N(R^c)_2$, $(CH_2)_{0-4}SO_2R^c$, $C_{1-4}$ alkyl and fluorinated $C_1$–$C_4$ alkyl; or are independently selected from halogen, cyano, $OR^c$, $N(R^c)_2$, $NR^cCOR^c$, $NR^cCON(R^c)_2$, $NR^cSO_2R^c$, $NR^cSO_2N(R^c)_2$, $(CH_2)_{0-4}CO_2R^c$, $(CH_2)_{0-4}CON(R^c)_2$, $(CH_2)_{0-4}SO_2N(R^c)_2$, $(CH_2)_{0-4}SO_2R^c$, $C_{1-4}$ alkyl and $CF_3$; or are independently selected from $CF_3$, cyano, halogen (e.g., fluorine), and $C_1$–$C_4$ alkyl.

In $R^8$, the substituents on the substituted naphthyl, pyridyl, pyrazinyl, thienyl, thiazolyl, furanyl, or quinazolinyl are independently selected from cyano, nitro, $N(R^c)_2$, $(CH_2)_{0-4}CO_2R^c$, $(CH_2)_{0-4}CON(R^c)_2$, $(CH_2)_{0-4}SO_2N(R^c)_2$, $(CH_2)_{0-4}SO_2R^c$, phenyl, $OR^c$, halogen, $C_1$–$C_4$ alkyl, fluorinated $C_1$–$C_4$ alkyl, $C_3$–$C_8$ cycloalkyl and fluorinated $C_3$–$C_8$ cycloalkyl; or are independently selected from cyano, nitro, $N(R^c)_2$, $(CH_2)_{0-4}CO_2R^c$, $(CH_2)_{0-4}CON(R^c)_2$, $(CH_2)_{0-4}SO_2N(R^c)_2$, $(CH_2)_{0-4}SO_2R^c$, phenyl, $OR^c$, halogen, $C_1$–$C_4$ alkyl and $CF_3$.

In one embodiment, $R^8$ is represented by the formula:

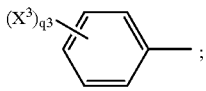

wherein $X^3$ and q3 are as defined above.

$R^9$ is hydrogen, $C_1$–$C_8$ alkyl, or fluorinated $C_1$–$C_8$ alkyl; or is hydrogen, $C_1$–$C_4$ alkyl, or fluorinated $C_1$–$C_4$ alkyl. In another embodiment, $R^2$ is hydrogen.

$R^{10}$ is hydrogen, cyano, $OR^c$, $CO_2R^c$, $CON(R^c)_2$, tetrazole, isooxadiazole, phenyl, substituted phenyl, naphthyl, substituted naphthyl, pyridyl, substituted pyridyl, thienyl, substituted thienyl, furanyl, or substituted furanyl; or is hydrogen, cyano, $OR^c$, $CO_2R^c$, $CON(R^c)_2$, phenyl, or mono- or di- or tri-substituted phenyl; or is hydrogen, cyano, $OR^c$, $CO_2R^c$, $CON(R^c)_2$, phenyl, or mono- or di-substituted phenyl; or is hydrogen, cyano, or $OR^c$.

In $R^{10}$, the substituents on the substituted phenyl are independently selected from halogen, cyano, nitro, $OR^c$, $(CH_2)_{0-4}CO_2R^c$, $(CH_2)_{0-4}CON(R^c)_2$, $N(R^c)_2$, $NR^cCOR^c$, $NR^cCON(R^c)_2$, $NR^cSO_2R^c$, $NR^cSO_2N(R^c)_2$, $(CH_2)_{0-4}SO_2N(R^c)_2$, $(CH_2)_{0-4}SO_2R^c$, $C_1$–$C_4$ alkyl and fluorinated $C_1$–$C_4$ alkyl; or are independently selected from halogen, cyano, $OR^c$, $(CH_2)_{0-4}CO_2R^c$, $(CH_2)_{0-4}CON(R^c)_2$, $N(R^c)_2$, $NR^cCOR^c$, $NR^cCON(R^c)_2$, $NR^cSO_2R^c$, $NR^cSO_2N(R^c)_2$, $(CH_2)_{0-4}SO_2N(R^c)_2$, $(CH_2)_{0-4}SO_2R^c$ and $C_1$–$C_4$ alkyl; or are independently selected from halogen, cyano, $OR^c$, $(CH_2)_{0-2}CO_2R^c$, $(CH_2)_{0-2}CON(R^c)_2$ and $C_1$–$C_4$ alkyl.

In $R^{10}$, the substituents on the substituted naphthyl, pyridyl, thienyl, or furanyl are independently selected from $(CH_2)_{0-4}CO_2R^c$, $(CH_2)_{0-4}CON(R^c)_2$, $(CH_2)_{0-4}SO_2N(R^c)_2$, $(CH_2)_{0-4}SO_2R^c$, phenyl, $OR^c$, halogen, $C_1$–$C_4$ alkyl, fluorinated $C_1$–$C_4$ alkyl and $C_3$–$C_8$ cycloalkyl; or are independently selected from $CF_3$, $(CH_2)_{0-4}CO_2R^c$, $(CH_2)_{0-4}CON(R^c)_2$, $(CH_2)_{0-4}SO_2N(R^c)_2$, $(CH_2)_{0-4}SO_2R^c$, phenyl, $OR^c$, halogen, $C_1$–$C_4$ alkyl and $C_3$–$C_8$ cycloalkyl.

In one embodiment, $R^{10}$ is represented by the formula:

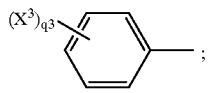

wherein $X^3$ and q3 are as defined above.

$R^{13}$, $R^{14}$, $R^{15}$ and $R^{16}$ are each independently selected from hydrogen, $C_1$–$C_8$ alkyl, fluorinated $C_1$–$C_8$ alkyl, $C_3$–$C_8$ cycloalkyl, fluorinated $C_3$–$C_8$ cycloalkyl, and $(CH_2)_{2-4}OR^c$; or are each independently selected from hydrogen, $C_1$–$C_4$ alkyl, fluorinated $C_1$–$C_4$ alkyl, and $(CH_2)_{2-4}OR^b$; or are each independently selected from hydrogen, $C_1$–$C_4$ alkyl and fluorinated $C_1$–$C_4$ alkyl; or are each independently selected from hydrogen, $C_1$–$C_4$ alkyl and $(CH_2)_{1-4}CF_3$; or are each independently selected from hydrogen and $C_1$–$C_4$ alkyl. In one embodiment, $R^{13}$, $R^{14}$, $R^{15}$ and $R^{16}$ are all hydrogen.

$R^{18}$ and $R^{20}$ are each independently selected from hydrogen and $OR^d$; or are each independently selected from hydrogen, hydroxy, methoxy, ethoxy, and $CF_3$; or are each independently selected from hydrogen and hydroxy (e.g., $R^{18}$ and $R^{20}$ are both hydrogen or both hydroxy).

$R^a$ is hydrogen, $C_1$–$C_8$ alkyl, fluorinated $C_1$–$C_8$ alkyl, or $C_3$–$C_8$ cycloalkyl; or is hydrogen, $C_1$–$C_4$ alkyl, or $(CH_2)_{0-3}CF_3$; or is hydrogen, methyl, ethyl, or $CF_3$; or is hydrogen, methyl, or ethyl.

$R^b$ is $C_1$–$C_8$ alkyl, fluorinated $C_1$–$C_8$ alkyl, $C_3$–$C_8$ cycloalkyl, or fluorinated $C_3$–$C_8$ cycloalkyl; or is $C_1$–$C_4$ alkyl or $(CH_2)_{0-3}CF_3$; or is methyl, ethyl, or $CF_3$; or is methyl or ethyl.

$R^c$ is hydrogen, $C_1$–$C_8$ alkyl, fluorinated $C_1$–$C_8$ alkyl, $C_3$–$C_8$ cycloalkyl, or fluorinated $C_3$–$C_8$ cycloalkyl; or is hydrogen, $C_1$–$C_4$ alkyl, or $(CH_2)_{0-3}CF_3$; or is hydrogen, methyl, ethyl, or $CF_3$; or is hydrogen, methyl, or ethyl.

$R^d$ is hydrogen, $C_1$–$C_8$ alkyl, $C_3$–$C_8$ cycloalkyl, or $(CH_2)_{0-4}CF_3$; or is hydrogen, $C_1$–$C_4$ alkyl, or $(CH_2)_{0-3}CF_3$; or is hydrogen, methyl, ethyl, or $CF_3$; or is hydrogen, methyl, or ethyl.

m, n, o, and p are each independently integers from 0 to 3; or from 0 to 2; or are 0 or 1. In other embodiments, m and n are each integers of from 0 to 3, wherein the sum of m+n is an integer of from 0 to 3; or m and n are each integers of from 0 to 2, wherein the sum of m+n is an integer of from 0 to 2; or m and n are each either 1 or 2 and the the sum of m+n is 1 or 2 (e.g., m=1 and n=1). In still other embodiments, o and p are each integers of from 0 to 3, wherein the sum of o+p is an integer of from 0 to 3; or o and p are each integers of from 0 to 2, wherein the sum of o+p is an integer of from 0 to 2; or o and p are each either 1 or 2, and the sum of o+p is either 1 or 2 (e.g., o=1 and p=1).

q1 is an integer from 0 to 5; or from 0 to 4; or from 0 to 3; or from 0 to 2; or is 0 or 1. In one embodiment, q1 is 2. In one aspect of the embodiment of q1=2, the substituted phenyl is either 2,4- or 3,4-di-substituted (e.g., 3,4-difluorophenyl).

t is an integer from 2 to 5; or from 2 to 4; or is 2 or 3; or is 2; or is 3.

u and v are each independently integers from 0 to 3; provided that u and v are not both zero; and further provided that when u is zero, Z is selected from $CH_2$, $CHF$, $CHR^b$, $C(R^b)_2$, $CF_2$, $CHCHF_2$ and $C=CF_2$.

w is an integer from 0 to 3, provided that when w is 0, $R^{20}$ is hydrogen. In other embodiments w is an integer from 0 to 2; or is 0 or 1; or is 0; or is 1.

Representative compounds of the present invention exhibit selectivity for the human alpha 1a adrenergic receptor. One implication of this selectivity is that these compounds display selectivity for lowering intraurethral pressure without substantially affecting diastolic blood pressure.

Representative-compounds of this invention display submicromolar affinity for the human alpha 1a adrenergic receptor subtype while displaying lower affinity for the human alpha 1d and alpha 1b adrenergic receptor subtypes, and many other G-protein coupled human receptors. Particular representative compounds of this invention exhibit nanomolar and subnanomolar affinity for the human alpha 1a adrenergic receptor subtype while displaying at least about 10 fold lower affinity for the human alpha 1d and alpha 1b adrenergic receptor subtypes, and many other G-protein coupled human receptors (e.g., serotonin, dopamine, alpha 2 adrenergic, beta adrenergic or muscarinic receptors). Still other compounds of this invention exhibit nanomolar and subnanomolar affinity for the human alpha 1a adrenergic receptor subtype while displaying at least about 20 fold lower affinity for the human alpha 1d and alpha 1b adrenergic receptor subtypes, in addition to exhibiting selectivity over other G-protein coupled human receptors (e.g., serotonin, dopamine, alpha 2 adrenergic, beta adrenergic or muscarinic receptors).

These compounds are administered in dosages effective to antagonize the alpha 1a receptor where such treatment is needed; e.g., treatment of BPH. For use in medicine, the salts of the compounds of this invention refer to non-toxic "pharmaceutically acceptable salts." Other salts may, however, be useful in the preparation of the compounds according to the invention or in the prepartion of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following:

Acetate, benzenesulfonate, benzoate, bicarbonate, bisulfate, bitartrate, borate, camsylate, carbonate, clavulanate, citrate, dihydrochloride, edetate, edisylate, estolate, esylate, fumarate, gluceptate, gluconate, glutamate, glycollylarsanilate, hexylresorcinate hydrobromide, hydrochloride, hydroxynaphthoate, hydroiodide, isothionate, lactate, lactobionate, laurate, malate, maleate, mandelate, mesylate, methylbromide, methylnitrate, methylsulfate, mucate, napsylate, nitrate, n-methylglucamine ammonium salt, oleate, palmitate, pantothenate, phosphate/diphosphate, polygalacturonate, salicylate, stearate, sulfate, subacetate, succinate, tannate, tartrate, tosylate and valerate.

Compounds of this invention are used to reduce the acute symptoms of BPH. Thus, compounds of this invention may be used alone or in combination with more long-term anti-BPH therapeutics, such as testosterone 5-a reductase inhibitors, including PROSCAR® (finasteride). Aside from their utility as anti-BPH agents, these compounds may be used to induce highly tissue-specific, localized alpha 1a adrenergic receptor blockade whenever this is desired. Effects of this blockade include reduction of intra-ocular pressure, control of cardiac arrhythmias, and possibly a host of alpha 1a receptor mediated central nervous system events.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient Conventional procedures for the selection and preparation of suitable prodrug derivatives are described, for example, in Design of Prodrugs, ed. H. Bundgaard, Elsevier, 1985.

The present invention further includes metabolites of the compounds of the present invention. Metabolites include active species produced upon introduction of compounds of this invention into the biological milieu.

Where the compounds according to the invention have at least one chiral center, they may accordingly exist as enantiomers. Where the compounds according to the invention possess two or more chiral centers, they may additionally exist as diastereoisomers. It is to be understood that all such isomers and mixtures thereof are encompassed within the scope of the present invention. Furthermore, some of the crystalline forms for compounds of the present invention may exist as polymorphs and as such are intended to be included in the present invention. In addition, some of the compounds of the present invention may form solvates with water (i.e., hydrates) or common organic solvents. Such solvates are also encompassed within the scope of this invention.

The term "selective alpha 1a adrenergic receptor antagonist," as used herein, refers to an alpha 1a antagonist compound which is at least about ten fold selective for the human alpha 1a adrenergic receptor as compared to the human alpha 1b, alpha 1d, alpha 2a, alpha 2b and alpha 2c adrenergic receptors.

The term "lower urinary tract tissue," as used herein, refers to and includes, but is not limited to, prostatic smooth muscle, the prostatic capsule, the urethra and the bladder neck.

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

The present invention includes pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt o f the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

As used herein, the term "composition" encompasses a product comprising the specified ingredients in the specified amounts, as well as any product which results, directly or indirectly, from combination of the specified ingredients in the specified amounts.

The liquid forms in which the novel compositions of the present invention may be incorporated for administration orally or by injection include aqueous solutions, suitably flavoured syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Where the processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known in the art.

The specificity of binding of compounds showing affinity for the alpha 1a receptor is shown by comparing affinity to membranes obtained from transfected cell lines that express the alpha 1a receptor and membranes from cell lines or tissues known to express other types of alpha (e.g., alpha 1d, alpha 1b) or beta adrenergic receptors. Expression of the cloned human alpha 1d, alpha 1b, and alpha 1a receptors and comparison of their binding properties with known selective antagonists provides a rational way for selection of compounds and discovery of new compounds with predictable pharmacological activities. Antagonism by these compounds of the human alpha 1a adrenergic receptor subtype may be functionally demonstrated in anesthetized animals. These compounds may be used to increase urine flow without exhibiting hypotensive effects.

The ability of compounds of the present invention to specifically bind to the alpha 1a receptor makes them useful for the treatment of BPH. The specificity of binding of compounds showing affinity for the alpha 1a receptor is compared against the binding affinities to other types of alpha or beta adrenergic receptors. The human alpha adrenergic receptor of the 1a subtype was recently identified, cloned and expressed as described in PCT International Application Publication Nos. WO94/08040, published Apr. 14, 1994 and WO 94/21660, published Sep. 29, 1994. The cloned human alpha 1a receptor, when expressed in mammalian cell lines, is used to discover ligands that bind to the receptor and alter its function. Expression of the cloned human alpha 1d, alpha 1b, and alpha 1a receptors and comparison of their binding properties with known selective antagonists provides a rational way for selection of compounds and discovery of new compounds with predictable pharmacological activities.

Compounds of this invention exhibiting human alpha 1a adrenergic receptor antagonism may further be defined by counterscreening. This is accomplished according to methods known in the art using other receptors responsible for mediating diverse biological functions. [See e.g., PCT International Application Publication No. WO94/10989, published May 26, 1994; U.S. Pat. No. 5,403,847, issued Apr. 4, 1995]. Compounds which are both selective amongst the various human alphal adrenergic receptor subtypes and which have low affinity for other receptors, such as the alpha 2 adrenergic receptors, the 3-adrenergic receptors, the muscarinic receptors, the serotonin receptors, the histamine receptors, and others are particularly preferred. The absence of these non-specific activities may be confirmed by using cloned and expressed receptors in an analogous fashion to the method disclosed herein for identifying compounds which have high affinity for the various human alphal adrenergic receptors. Furthermore, functional biological tests are used to confirm the effects of identified compounds as alpha 1a adrenergic receptor antagonists.

The present invention also has the objective of providing suitable topical, oral, systemic and parenteral pharmaceutical formulations for use in the novel methods of treatment of the present invention. The compositions containing compounds of this invention as the active ingredient for use in the specific antagonism of human alpha 1a adrenergic receptors can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an alpha 1a antagonistic agent.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

Compounds of this invention may be administered in any of the foregoing compositions and according to dosage regimens established in the art whenever specific blockade of the human alpha 1a adrenergic receptor is required.

The daily dosage of the products may be varied over a wide range; e.g., from about 0.01 to about 1000 mg per adult human per day. For oral administration, the compositions are preferably provided in the form of tablets containing 0.01, 0.05, 0.1, 0.5, 1.0, 2.5, 5.0, 10.0, 15.0, 25.0, 50.0 and 100 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. An effective amount of the drug is ordinarily supplied at a dosage level of from about 0.0002 mg/kg to about 20 mg/kg of body weight per day. Preferably, the range is from about 0.001 to about 10 mg/kg of body weight per day, and especially from about 0.001 mg/kg to about 7 mg/kg of body weight per day. The compounds may be administered on a regimen of 1 to 4 times per day.

Compounds of this patent disclosure may be used alone at appropriate dosages defined by routine testing in order to obtain optimal antagonism of the human alpha 1a adrenergic receptor while minimizing any potential toxicity. In addition, co-administration or sequential administration of other agents which alleviate the effects of BPH is desirable. Thus, in one embodiment, this invention is administration of compounds of this invention and a human testosterone 5-a reductase inhibitor. Included with this embodiment are inhibitors of 5-alpha reductase isoenzyme 2. Many such compounds are now well known in the art and include such compounds as PROSCAR®, (also known as finasteride, a 4-Aza-steroid; see U.S. Pat. Nos. 4,377,584 and 4,760,071, for example). In addition to PROSCAR®, which is principally active in prostatic tissue due to its selectivity for human 5-a reductase isozyme 2, combinations of compounds which are specifically active in inhibiting testosterone 5-alpha reductase isozyme 1 and compounds which act as dual inhibitors of both isozymes 1 and 2, are useful in combination with compounds of this invention. Compounds that are active as 5a-reductase inhibitors have been described in WO93/23420, EP 0572166; WO 93/23050; WO93/23038; WO93/23048; WO93/23041;WO93/23040; WO93/23039; WO93/23376; WO93/23419, EP 0572165; WO93/23051.

The dosages of the alpha 1a adrenergic receptor and testosterone 5-alpha reductase inhibitors are adjusted when combined to achieve desired effects. As those skilled in the art will appreciate, dosages of the 5-alpha reductase inhibitor and the alpha 1a adrenergic receptor antagonist may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Thus, in one embodiment of the present invention, a method of treating BPH is provided which comprises administering to a subject in need of treatment any of the compounds of the present invention in combination with finasteride effective to treat BPH. The dosage of finasteride administered to the subject is from about 0.01 mg per subject per day to about 50 mg per subject per day in combination with an alpha 1a antagonist. In one aspect, the dosage of finasteride in the combination is from about 0.2 mg per subject per day to about 10 mg per subject per day, and, in another aspect, from about 1 to about 7 mg per subject to day (e.g., about 5 mg per subject per day).

For the treatment of benign prostatic hyperplasia, compounds of this invention exhibiting alpha 1a adrenergic receptor blockade can be combined with a therapeutically effective amount of a 5a-reductase 2 inhibitor, such as finasteride, in addition to a 5a-reductase 1 inhibitor, such as 4,7β-dimethyl-4-aza-5a-cholestan-3-one, in a single oral, systemic, or parenteral pharmaceutical dosage formulation. Alternatively, a combined therapy can be employed wherein the alpha 1a adrenergic receptor antagonist and the 5a-reductase 1 or 2 inhibitor are administered in separate oral, systemic, or parenteral dosage formulations. See, e.g., U.S. Pat. No. 4,377,584 and U.S. Pat. No. 4,760,071 which describe dosages and formulations for 5a-reductase inhibitors.

Abbreviations used in the instant specification, particularly the Schemes and Examples, are as follows:

DIPEA=diisopropyl ethylamine
DMF=N,N-dimethylformamide
DMSO=dimethylsulfoxide
EDTA=ethylenediamine tetraacetic acid
Et=ethyl
Et$_2$O=diethyl ether
EtOAc=ethyl acetate
FAB MS=fast atom bombardment mass spectroscopy
LDA=lithium diisopropyl amide
LHMDS=lithium bis(trimethylsilyl)amide
Me=methyl
MeOH=methanol
NMR=nuclear magnetic resonance
PCTLC=preparative centrifugal thin layer chromatography
PMBCl=p-methoxybenzyl chloride
(p-NO$_2$Ph)COCl=p-nitrophenylchloroformate
TFA=trifluoroacetic acid
THF=tetrahydrofuran The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Many of the compounds of the present invention can be prepared via Scheme 1 shown below. In Scheme 1, the ortho-aminoaryl- or o-aminoheteroaryl-nitrile 1 is treated with an arylmagnesium bromide or an aryllithium, followed by diethylcarbonate to afford aryl-substituted polyazanaphthalenone 2 (e.g., 4-aryl-quinazolin-2-one or 4-aryl-pteridin-2-one). Compound 2 is then reacted either with LHMDS and 4-methoxybenzyl chloride or with LHMDS and R^D (wherein R^ is C$_1$–C$_8$ alkyl or fluorinated C$_1$–C$_8$ alkyl, and D is chloro, bromo, iodo, mesylate, tosylate, nosylate, or triflate) to form nitrogen-alkylated analog 3. Compound 3 is reacted either with R$^1$ Cu (other than R$^1$=H) or with NaBH$_4$ (to give R$^1$=H) to form dihydro derivative 4. Deprotonation of 4 with a strong base (for example, LDA) and addition to a THF solution of p-nitrophenylchloroformate produces stable, isolable "activated" dihydro polyazanaphthalenone 5, which is coupled with amines of formula Q—H to give coupled product 6, which for R*=R^ (=R$^2$ other than H) is a compound of the invention 7a. For R*=PMB, coupled product 6 is deprotected to afford 7b (i.e., R$^2$=H).

Methods for preparing the amines of formula Q—H are described in U.S. Pat. No. 5,661,163, WO 98/57632, WO 98/57638, WO 98/57639, WO 98/57640, WO 98/57641 and WO 98/57642.

Scheme 2 illustrates the preparative procedures employed in Examples 1–6 below.

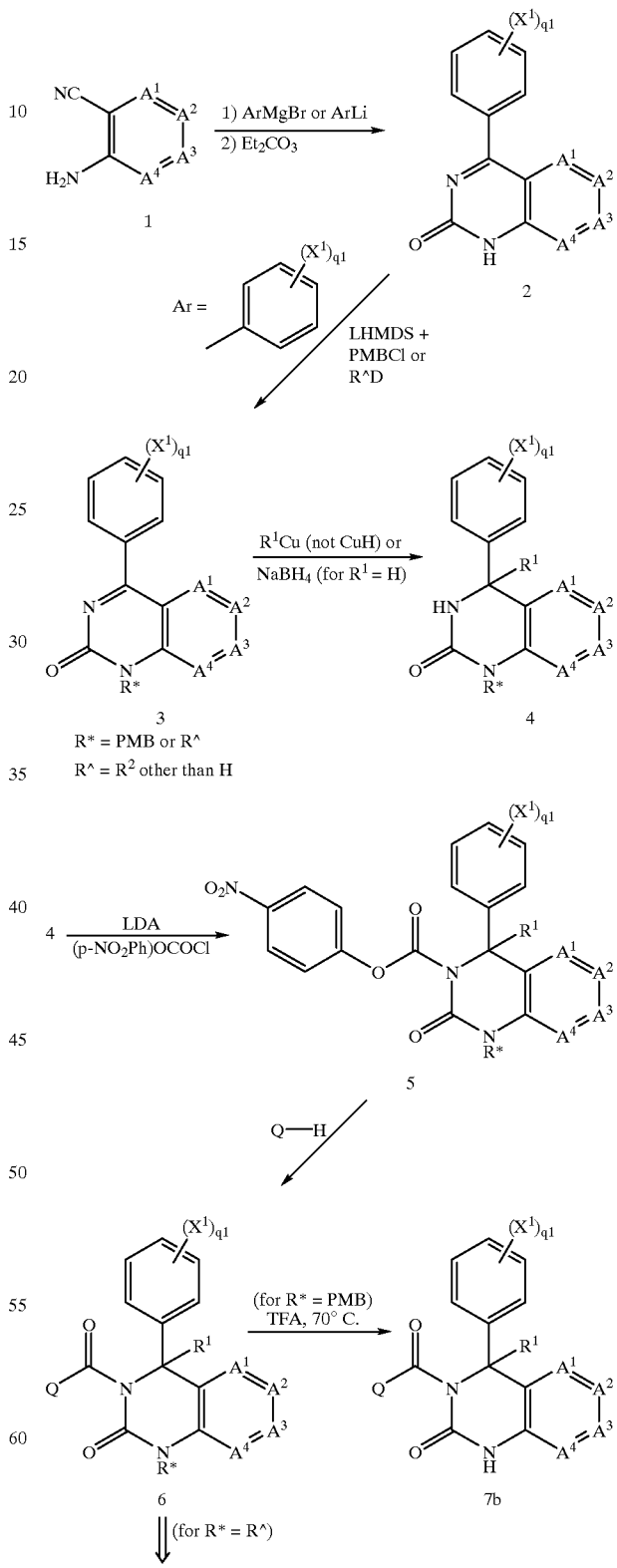

-continued
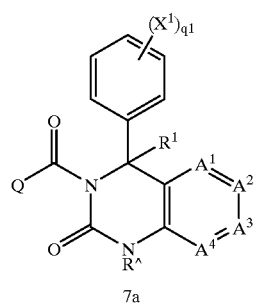
7a
SCHEME 2
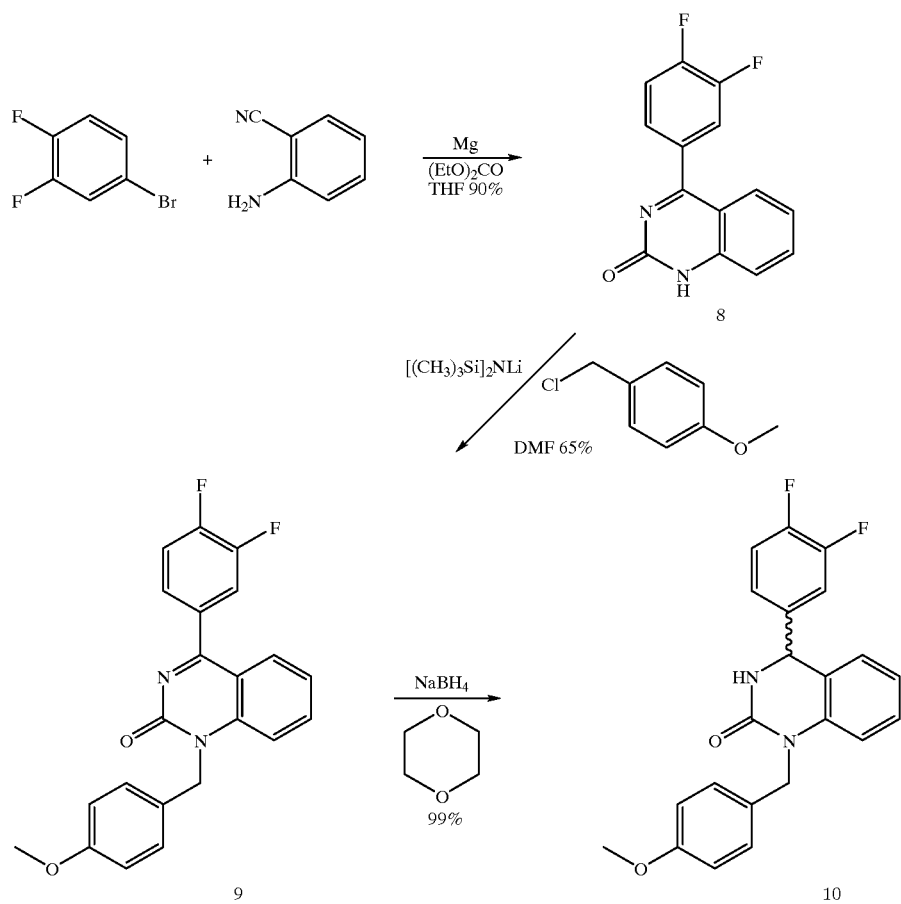

-continued
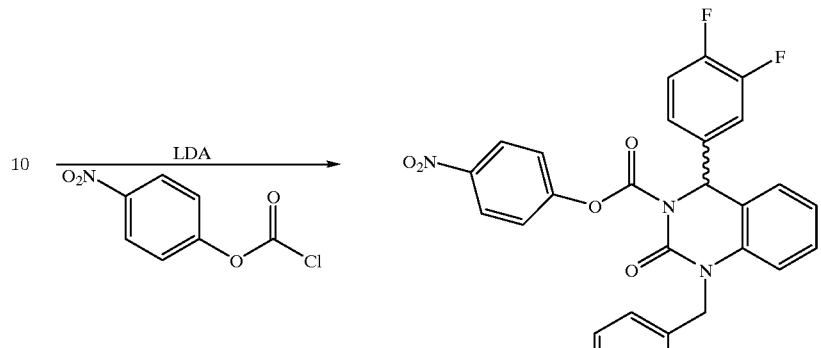
11
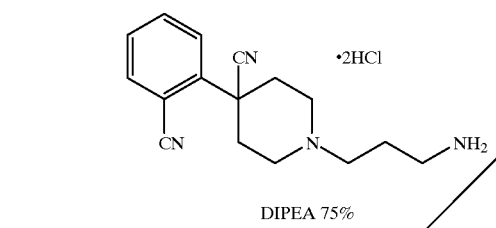
DIPEA 75%
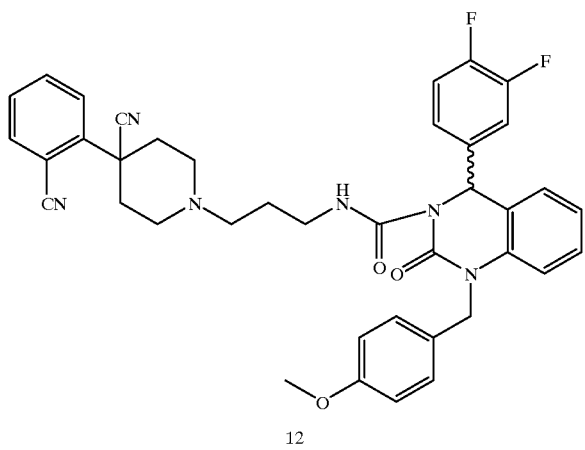
12
12 →(TFA, 65° C., 81%)
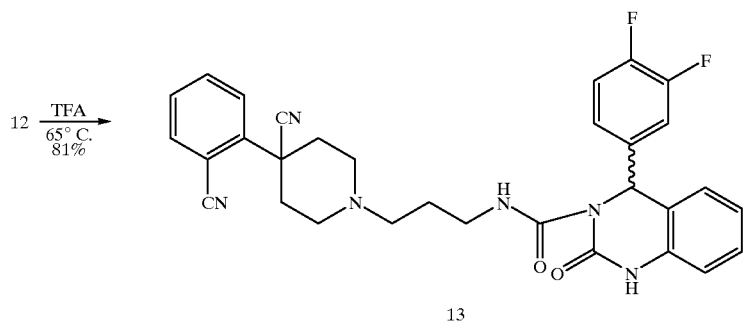
13

The following Examples further describe and illustrate the invention and its practice and are not to be construed as limiting the scope or spirit of the invention.

EXAMPLE 1

N-(3-Amino)propyl-4-(2-cyanophenyl)-4-cyanopiperidine Dihydrochloride

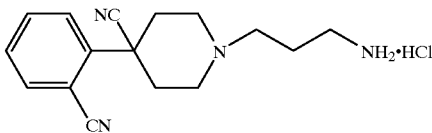

Step A: Bis(2-chloroethyl)-N-(1,1-dimethylethoxy)carbonyl Amine

A solution of N-(2,2'-bischloro)diethyl amine (23.0 g, 0.130 mol) and di-tert-butyl dicarbonate (28.8 g, 0.130 mol) in $CH_2Cl_2$ (150 mL) was treated with N,N-diisopropylethylamine (22.52 ml, 0.720 mol) at room temperature (1.5 h). The solvent was removed in vacuo and the residue was triturated with ether (300 ml). The ether solution was collected and concentrated in vacuo affording N-(2,2'-bischloro)-diethyl-N-(1,1-dimethylethoxy)carbonyl amine as a clear oil.

$^1$H NMR ($CDCl_3$): δ 3.65 (m, 8H), 1.52 (s, 9H); FAB MS (3:1 mixture of dithiothreitol and dithioerythritol in MeOH) m/e 242 g/mole ($M^+$+H, $C_{25}H_{29}N_2O_5SCl$=242.2 g/mole.).

Step B: 4-Cyano-N-(1,1-dimethylethoxy)carbonyl-4-(2-cyanophenyl)piperidine

A solution of bis(2-chloroethyl)-N-(1,1-dimethylethoxy)carbonyl amine (19 g, 78 mmol) and homophthalonitrile (8.6 g, 60 mmol) and cesium carbonate (79 g, 241 mmol) was stirred at 60° C. for 12 hours. The solution cooled to room temperature and diluted with 500 ml EtOAc and washed with saturated aqueous $NaHSO_4$ and saturated aqueous NaCl. The solution was dried over $Na_2SO_4$, concentrated in vacuo, and purified by PCTLC (30% EtOAc in Hexane) to afforded 4-cyano-N-(1,1-dimethylethoxy)carbonyl-4-(2-cyanophenyl)piperidine as a yellow/orange oil.

$^1$H NMR ($CDCl_3$): δ 7.81–7.79 (d, 2H), 7.67–7.65 (m, 2H), 7.51–7.47 (m, 1H), 4.31 (br s, 2H), 3.26 (br s, 2H), 2.33–2.20 (m, 4H), 1.48 (s, 9H).

Step C: 4-Cyano-4-(2-cyanophenyl)piperidine Hydrochloride

A solution of EtOAc saturated with HCl (200 ml) was added to 4-cyano-N-(1,1-dimethylethoxy)carbonyl-4-(2-methylphenyl)piperidine (1.5 g, 5.7 mmol). The resulting mixture was allowed to react for 1 hour at room temperature. The EtOAc was removed in vacuo affording 1.5 g of 4-cyano-4-(2-cyanophenyl)piperidine hydrochloride as a yellow solid.

Step D: 4-(2-Cyanophenyl)-4-cyano-N-(3-[N-{1,1-dimethylethoxycarbonyl}]amino)propylpiperidine A solution of 4-(2-cyanophenyl)-4-cyanopiperidine hydrochloride (0.5 g, 2.01 mmol) and N,N-diisopropylethylamine (0.421 ml, 2.42 mmol) in DMF (5 mL) at 0° C. was added sodium hydride (0.0968 g, 2.42 mmol). The slurry stirred for 1 hour at 0° C. and was then added N-(3-bromopropyl)-N-(1,1-dimethylethoxy)carbonyl amine (0.480 g, 2.01 mmol) in DMF (3 mL). The solution stirred for 12 hours at room temperature. The reaction was quenched by the addition of water. The product was extracted with EtOAc (2×50 ml) and washed with $H_2O$ (2×25 ml). The solvent was dried over $Na_2SO_4$, concentrated in vacuo, and purified by PCTLC (5% MeOH in $CHCl_3$). 4(2-Cyanophenyl)4-cyano-N-[3-{N-(1,1-dimethylethoxy)carbonyl}amino]propyl piperidine was obtained as an oil.

$^1$H NMR ($CDCl_3$): δ 7.80–7.78 (dd, 1H), 7.67–7.59 (m, 2H), 7.49–7.45 (m, 1H), 5.14 (br s, 1H), 3.21–3.20 (d, 2H), 3.09–3.06 (d, 2H), 2.58–2.51 (m, 3H), 2.43–2.40 (d, 2H), 2.30–2.25 (m, 2H), 1.73–1.66 (m, 2H,), 1.56 (s, 1H), 1.43 (s, 9H).

Step E: N-(3-Amino)propyl-4-(2-cyanophenyl)-4-cyanopiperidine Dihydrochloride

The title compound was prepared using the same procedure desribed above in Step C for the preparation of 4-cyano-4-(2-cyanophenyl)piperidine hydrochloride.

EXAMPLE 2

3-[4-(4-Fluorophenyl)piperidin-1-yl]propylamine

Step A. 4-(4-Fluorophenyl)piperidine Hydrochloride

To a solution of 4-(4-fluorophenyl)-1,2,3,6-tetrahydropyridine hydrochloride (10 g) in methanol (200 mL) was added 10% palladium on charcoal (0.5 g) and the mixture was hydrogenated at 50 psi for 3 h. The catalyst was removed by filtration and solvent was evaporated to leave the product as a white powder, which was used in the next step without any purification. C M.P. 181–182 C. $^1$H NMR ($CDCl_3$): δ 1.95–2.03 (br d, 2H), 2.14–2.29 (m, 2H), 2.70–2.80 (m, 1H), 2.91–3.07 (br q, 2H), 3.60–3.64 (br d, 2H), 6.96–7.03 (m, 2H), 7.19–7.22 (m, 2H), 9.60 (br s, 1H), 9.71 (br s, 1H).

Step B. 3-[4-(4-Fluorophenyl)piperidin-1-yl]propylphthalimide

A mixture of 4-(4-fluorophenyl)piperidine hydrochloride (5.08 g, 23.2 mmol), 3-bromopropylphthalimide (6.22 g, 23.2 mmol), and potassium carbonate (15 g) in DMF (100 mL) was stirred and heated at 95–100 C for 12 h. About 80% of the solvent was evaporated at reduced pressure, the residue was diluted with ethyl acetate (200 mL) and washed with brine (3×100 mL) and dried ($Na_2SO_4$). Solvent was evaporated and the residue was purified by column chromatography on silica gel using 1/1 hexane-ethyl acetate to 100% ethyl acetate as eluent. This product was crystallized from isopropanol to give a white crystalline solid; m.p. 80–81 C. This material was used in the next step. Concentration of the mother liquor and cooling gave the second crop.

$^1$H NMR ($CDCl_3$): δ 1.43–1.52 (m, 2H), 1.67–1.75 (m, 2H), 1.80–1.96 (m, 4H), 2.33–2.46 (m, 3H), 2.94–2.99 (br d, 2H), 3.78 (t, J=7 Hz, 2H), 6.90–7.04 (m, 4H), 7.70–7.74 (m, 2H), 7.84–7.87 (m, 2H).

Step C. 3-[4-(4-Fluorophenyl)piperidin-1-yl]propylamine

To a solution of 3-[4-(4-fluorophenyl)piperidin-1-yl] propylphthalimide (4.5 g, 12.3 mmol) in methanol (200 mL) was added 4 ml of hydrazine and the mixture was refluxed for 8 h. It was cooled, and the white solid was filtered and washed with methanol (20 mL). Solvent was evaporated, and the residue was dried under vacuum for 4 h. Chloroform (50 mL) was added to this material, it was stirred for 1 h and filtered. The white solid was washed with more chloroform (20 mL), and the solvent was evaporated from the combined filtrates to leave the crude product as an oil. It was purified by column chromatography on silica gel using dichloromethane/methanol/2 M ammonia in methanol (10/3/1) as the eluent.

¹H NMR (CDCl₃): δ 1.60–1.83 (m, 6H), 1.96–2.07 (m, 4H), 2.40–2.55 (m, 3H), 2.70–2.85 (br t, 2H), 3.03–3.07 (br d, 2H), 6.93–7.00 (m, 2H), 7.14–7.20 (m, 2H).

EXAMPLE 3

4-(3,4-Difluorophenyl)-quinazolin-2-one (8)

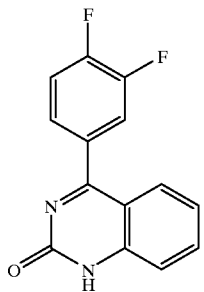

An oven dried round-bottom flask was charged with magnesium turnings (3.55 g, 146 mmol) in THF (100 mL) under argon. 1-Bromo-3,4-difluorobenzene (4.0 mL, 35.3 mmol) was added to the suspension in one portion. The solution was heated to 40° C. Once the temperature had stabilized at 50° C., the remainder of the bromide (13.52 mL, 155 mmol total) was added dropwise. After complete addition, the solution was stirred for 1 hour at 65° C. A solution of anthranilonitrile (4.95 g, 41.9 mmol) in THF (25 mL) was added dropwise while keeping the internal temperature constant. After stirring or two hours at 65° C., diethyl carbonate (16.3 mL, 135 mmol) was added dropwise to the brownish-red solution . This solution was stirred for an additional 30 minutes at 65° C. and then cooled to room temperature. The solution was poured into a mixture of 250 mL of 1 M citric acid and ice. The mixture was extracted three times with CHCl₃ (50 mL) and the combined extracts were washed with a 10% Na₂CO₃ solution. The organics were dried over Na₂SO₄, concentrated, and triturated with Et₂O to afford the title compound.

¹H NMR (DMSO-d₆, 400 MHz) 7.81–7.72 (m, 2H), 7.69–7.62 (m, 2H), 7.57–7.53 (m, 1H), 7.38–7.36 (d, 1H), 7.23–7.19 (t, 1H).

EXAMPLE 4

4-(3,4-Difluorophenyl)-1-(4-methoxybenzyl)-quinazolin-2-one (9)

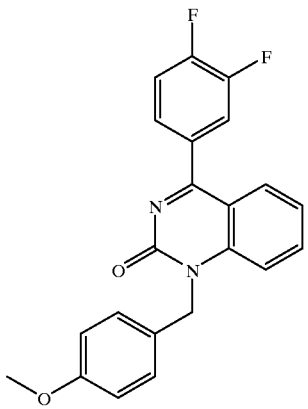

To a 0° C. solution of 8 (9.73 g, 37.7 rnmol) in DMF (100 mL) under argon was added lithium bis(trimethylsilyl)amide (43.9 mL, 1.0 M) dropwise. 4-Methoxybenzyl chloride (8.52 mL, 62.8 mmol) was then added in one portion. The solution was stirred at 55° C. for sixteen hours. The solvent was removed in vacuo and the residue was partitioned between CHCl₃ and cold 1.0 M citric acid. The aqueous layer was extracted with CHCl₃, and the combined organic extracts were washed with 10% Na₂CO₃ and dried. The crude product was not purified. A light yellow solid was obtained.

¹H NMR (DMSO-d₆, 400 MHz) 7.86–7.64 (m, 4H), 7.59–7.57 (d, 2H), 7.30–7.27 (m, 3H), 6.90–6.88 (d, 2H), 5.46 (s, 2H), 3.71 (s, 3H).

EXAMPLE 5

4-(3,4-Difluorophenyl)-1-(4-methoxybenzyl)-3,4-dihydro-quinazolin-2-one (10)

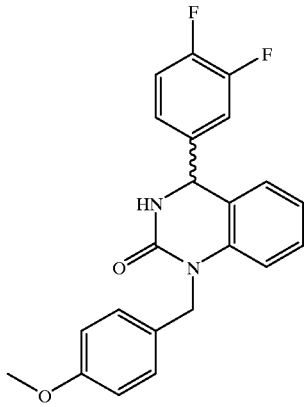

To a 0° C. solution of 9 (9.33 g, 24.6 mmol) in dioxane (250 mL) was added NaBH₄ (1.02 g, 27.1 mmol) in one portion. The solution stirred for two hours at room temperature. The solvent was removed in vacuo, and the residue was partitioned between CHCl₃ and 1 N HCl. The aqueous layer was extracted with CHCl₃, and the combined organic extracts were dried, concentrated, and purified by PCTLC (1:1 EtOAc:Hex). A white solid was obtained. $^1$H NMR (CDCl$_3$, 400 MHz) 7.30–7.04 (m, 6H), 6.93–6.83 (m, 6H), 5.58 (s, 1H), 5.18–5.04 (q, 2H), 3.77 (s, 3H).

EXAMPLE 6

4-(3,4-Difluorophenyl)-1-(4-methoxybenzyl)-3-(4-nitrophenoxycarbonyl)-3,4-dihydro-quinazolin-2-one (11)

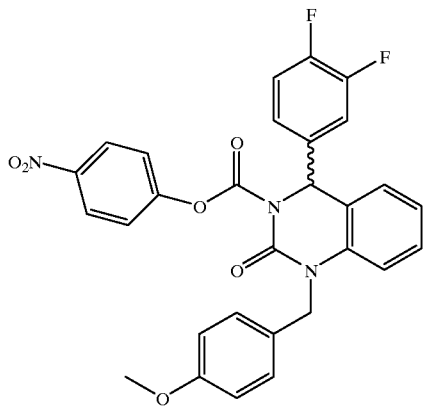

The title compound was prepared by treating 10 (0.292 g, 0.767 mmol) with lithium diisopropylamide (2.0 M THF solution, 1.1 equivalents) in THF at –78° C. for 20 minutes followed by the rapid addition of 4-nitrophenyl chloroformate (1.5 equivalents) in THF. The $^1$H NMR was consistent with the assigned structure.

EXAMPLE 7

4-(3,4-Difluorophenyl)-1-(4-methoxybenzyl)-3-((4-cyano-4-(2-cyanophenyl)piperidin-1-yl)propylcarbamoyl)-3,4-dihydro-quinazolin-2-one (12)

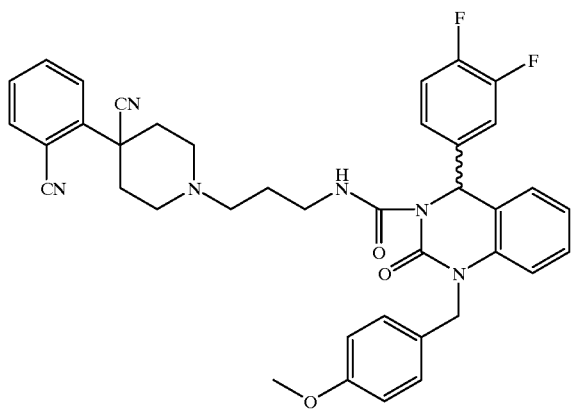

To a solution of 11 (0.060 g, 0.109 mmol) in 10 ml of CHCl$_3$ was added N-(3-amino)propyl-4-(2-cyanophenyl)-4-cyanopiperidine dihydrochloride (Example 1) and diisopropyl ethylamine (0.057 mL, 0.329 mmol). The resulting solution was stirred for 2 hours and the crude material purified by PCTLC (5% MeOH in CHCl$_3$/2%NH$_4$OH) affording the title compound.

$^1$H NMR (CDCl$_3$, 400 MHz) 9.10–9.07 (t, 1H), 7.78–7.76 (d, 1H), 7.54–7.48 (m, 3H), 7.13–7.09 (t, 1H), 7.02–6.93 (q, 1H), 6.91–6.83 (m, 5H), 6.75–6.73 (d, 2H), 5.05–5.01 (d, 1H), 4.88–4.84 (d, 2H), 3.77 (s, 3H) 3.49–3.45 (m, 3H), 3.12–3.03 (m, 2H), 2.57–2.51 (m, 4H), 2.38–2.35 (d, 3H), 2.26–2.23 (m, 1H), 1.82–1.77 (m, 2H), 1.53 (s, 2H). MS (FAB) 675.4 (M+1); Analysis calculated for C$_{39}$H$_{36}$N$_6$O$_3$F$_2$: C:69.42, H:5.37, N:12.45, Found C:69.43, H:5.36, N:12.14.

EXAMPLE 8

4-(3,4-Difluorophenyl)-3-((4-cyano-4-(2-cyanophenyl)piperidin-1-yl)propylcarbamoyl)-3,4-dihydro-quinazolin-2-one (13)

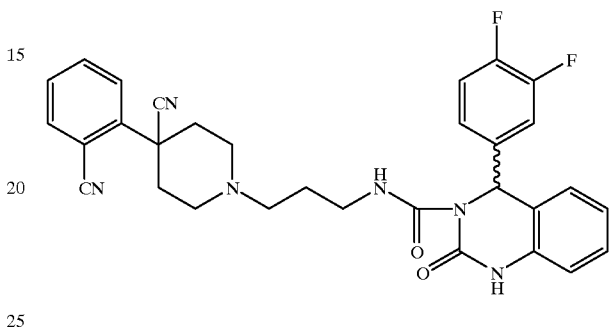

A solution of 12 (0.050 g, 0.074 mmol) in TFA (1.5 mL) was stirred for six hours at 65° C. The solvent was removed in vacuo and azeotroped twice with toluene. The product was then purified by PCTLC (5% MeOH in CHCl$_3$/2%NH$_4$OH). A white solid was obtained.

$^1$H NMR (CDCl$_3$, 400 MHz) 9.06–9.04 (t, 1H), 7.79–7.77 (d, 1H), 7.66–7.58 (m, 2H), 7.48–7.44 (t, 1H), 7.40 (s, 1H), 7.30–7.23 (m, 2H), 7.11–6.98 (m, 4H), 6.89 (s, 1H), 6.85–6.83 (d, 1H), 3.46–3.37 (m, 2H) 3.07–3.04 (m, 2H), 2.58–2.51 (m, 4H), 2.40–2.27 (m, 4H), 1.81–1.76 (m, 2H). MS (FAB) 555.2 (M+1); Analysis calculated for C$_{31}$H$_{28}$N$_6$O$_2$F$_2$.50 EtOAc: C:66.20, H:5.39, N:14.04, Found C:65.87, H:5.15, N:14.07.

EXAMPLE 9

4-(3,4-Difluorophenyl)-1-(4-methoxybenzyl)-3-(4-(4-fluorophenyl)piperidin-1-yl)propylcarbamoyl)-3,4-dihydro-quinazolin-2-one (14)

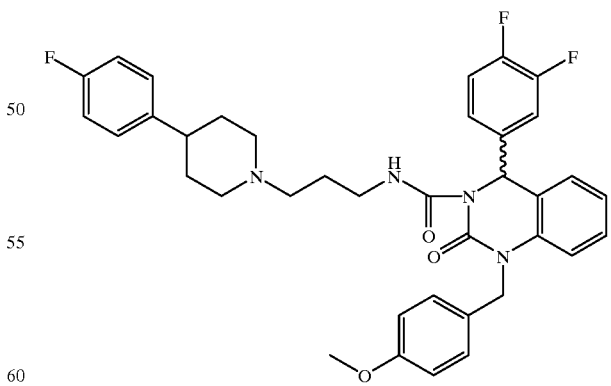

The title compound was prepared using the same procedure described for the preparation of 12, except that 3-[4-(4-fluorophenyl)piperidin-1-yl]propylamine (Example 2) was used in place of N-(3-amino)propyl-4-(2-cyanophenyl)-4-cyanopiperidine dihydrochloride.

¹H NMR (CDCl₃, 400 MHz) 9.03–9.00 (t, 1H), 7.30–7.24 (q, 2H), 7.17–7.09 (m, 3H), 7.04–6.91 (m, 7H), 6.88–6.82 (m, 2H), 6.76–6.74 (d, 2H), 5.17–5.13 (d, 1H), 4.95–4.91 (d, 1H), 3.45–3.41 (q, 2H) 3.05–3.03 (m, 2H), 2.46–2.42 (t, 3H), 2.03–1.97 (m, 2H), 1.82–1.76 (m, 6H). MS (FAB) 643.3 (M+1); Analysis calculated for $C_{37}H_{37}N_4O_3F_2 \cdot 60$ HCl+1.05 CHCl₃: C:57.85, H:4.93, N:7.09, Found C:57.86, H:5.31, N:6.71.

EXAMPLE 10

4-(3,4-Difluorophenyl)-3-(4-(4-fluorophenyl) piperidin-1-yl)propylcarbamoyl)-3,4-dihydro-quinazolin-2-one (15)

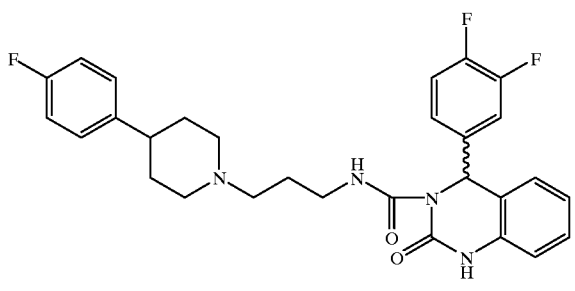

The title compound was prepared using the same procedure described for the preparation of 13.

¹H NMR (CDCl₃, 400 MHz) 9.04–9.01 (t, 1H), 7.55 (s, 1H), 7.31–7.24 (m, 2H), 7.17–7.02 (m, 5H), 7.00–6.94 (m, 3H), 6.90–6.83 (m, 2H), 3.44–3.37 (m, 2H) 3.05–3.02 (d, 2H), 2.47–2.42 (m, 3H), 2.07–2.00 (m, 2H), 1.82–1.73 (m, 6H). MS (FAB) 523.3 (M+1); Analysis calculated for $C_{29}H_{29}N_4O_2F_3$ 1.45 HCl+0.35 EtOAc: C:60.22, H:5.53, N:9.24, Found C:60.21, H:5.64, N:9.32.

EXAMPLE 11 trans-4-(3,4-Difluorophenyl)-3-(1-(4-(2-cyanophenyl)cyclohexyl)-3-hydroxy-azetidin-3-yl) methylcarbamoyl)-3,4-dihydro-quinazolin-2-one (16)

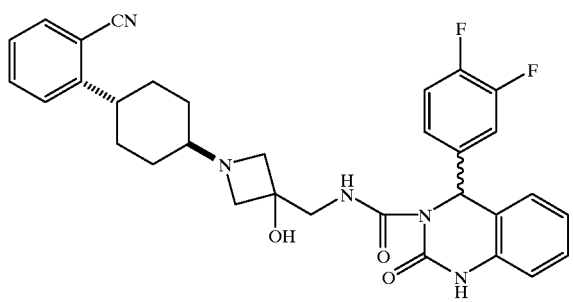

The title compound was prepared using a procedure analogous to that described for the preparation of 13, except that trans-1-(4-( 2-cyanophenyl)cyclohexyl)-3-hydroxy-azetidin-3-yl)methylamine was used in place of N-(3-amino)propyl-4-(2-cyanophenyl)-4-cyanopiperidine dihydrochloride. 1-(4-(2-Cyanophenyl)cyclohexyl)-3-hydroxy-azetidin-3-yl)methylamine was prepared in accordance with procedures described in WO 98/57641.

¹H NMR (CDCl₃, 400 MHz) 9.58–9.55 (t, 1H), 8.83 (br s, 1 H), 7.63–7.61 (d, 1H), 7.57–7.53 (t, 1H), 7.37–7.35 (d, 1H), 7.31–7.26 (m, 3H), 7.23–7.21 (d, 1H), 7.09–7.01 (m, 3H), 6.98–6.91 (m, 2H), 6.84 (s, 1H) 3.62–3.61 (d, 2H) 3.41–3.37 (m, 2H), 3.29–3.25 (m, 2H), 3.06–3.00 (t, 1H), 2.18 (s, 1H), 1.98–1.88 (m, 4H), 1.51–1.43 (m, 2H), 1.36–1.33 (m, 2H). MS (FAB) 572.1 (M+1); Analysis calculated for $C_{32}H_{31}N_5O_3F_2 \cdot 15$ CH₂Cl₂+0.05 Et₂O C:66.07, H:5.45, N:11.91, Found C:65.95, H:5.37, N:11.87.

EXAMPLE 12 trans-4-(3,4-Difluorophenyl)-3-(1-(4-(2-cyanophenyl)cyclohexyl)azetidin-3-l) methylcarbamoyl)-3,4-dihydro-quinazolin-2-one (17)

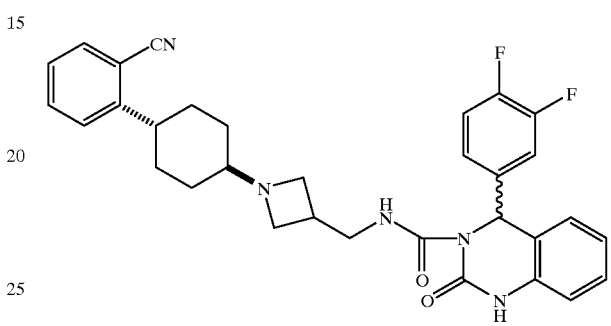

The title compound was prepared using a procedure analogous to that described for the preparation of 13, except that trans-1-(4-(2-cyanophenyl)cyclohexyl)azetidin-3-ylmethylamine was used in place of N-(3-amino)propyl-4-(2-cyanophenyl)-4-cyanopiperidine dihydrochloride. 1-(4-(2-Cyanophenyl)cyclohexyl) azetidin-3-ylmethylamine was prepared in accordance with procedures described in WO 98/57641.

¹H NMR (CDCl₃, 400 MHz) 9.15–9.12 (t, 1H), 7.90 (br s, 1H), 7.60–7.58 (d, 1H), 7.54–7.50 (t, 1H), 7.33–7.23 (m, 4H), 7.12–6.96 (m, 4H), 6.89–6.85 (t, 2H), 3.53–3.48(m, 2H) 3.41–3.38 (t, 2H), 2.98–2.87 (m, 3H), 2.72–2.68 (m, 1H), 2.07–2.01 (m, 1H), 1.92–1.90 (m, 4H), 1.54–1.45 (m, 2H), 1.22–1.17 (m, 2H). MS (FAB) 556.1 (M+1); Analysis calculated for $C_{32}H_{31}N_5O_2F_2 \cdot 35$ CH₂Cl₂+0.20 Et₂O C:66.34, H:5.66, N:11.67, Found C:66.47, H:5.61, N:11.66.

EXAMPLE 13 trans-4-(3,4-Difluorophenyl)-3-(1-(4-(2-pyridyl) cyclohexyl)azetidin-3-yl)methylcarbamoyl)-3,4-dihydro-quinazolin-2-one (18)

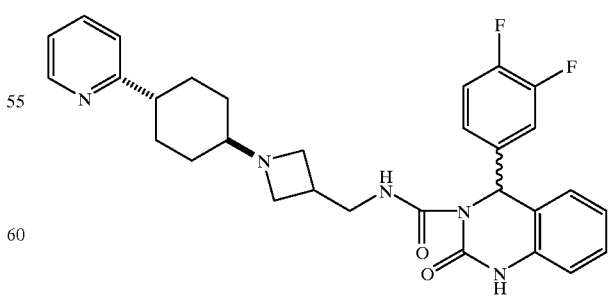

The title compound was prepared using a procedure analogous to that described for the preparation of 13, except that trans-1-(4-(2-pyridyl)cyclohexyl)azetidin-3-ylmethyl amine was used in place of N-(3-amino)propyl-4-(2-cyanophenyl)-4-cyanopiperidine dihydrochloride. 1-(4-(2-Pyridyl)cyclohexyl)azetidin-3-ylmethyl amine was prepared in accordance with procedures described in WO 98/57641.

$^1$H NMR (CDCl$_3$, 400 MHz) 9.13–9.1 (t, 1H), 8.52–8.50 (d, 1H), 8.00 (br s, 1H), 7.60–7.56 (m, 1H), 7.30–7.22 (m, 2H), 7.13–6.98 (m, 6H), 6.87–6.48 (t, 2H), 3.54–3.48 (m, 2H) 3.42–3.38 (t, 2H), 2.98–2.94 (m, 3H), 2.72–2.61 (m, 2H), 204–1.88 (m, 5H), 1.56–1.53 (q, 2H), 1.14–1.10 (m, 2H). MS (FAB) 532.1 (M+1); Analysis calculated for C$_{30}$H$_{31}$N$_5$O$_2$F$_2$.45 CH$_2$Cl$_2$+0.25 Et$_2$O C:64.20, H:5.89, N:11.90, Found C:64.18, H:5.71, N:11.91.

EXAMPLE 14

As a specific embodiment of an oral composition, 100 mg of the compound of Example 10 is formulated with sufficient finely divided lactose to provide a total amount of 580 to 590 mg to fill a size O hard gel capsule.

EXAMPLE 15

Screening Assay: Alpha 1a Adrenergic Receptor Binding

Membranes prepared from the stably transfected human alpha 1a cell line (ATCC CRL 11140) were used to identify compounds that bind to the human alpha 1a adrenergic receptor. These competition binding reactions (total volume=200 µl) contained 50 mM Tris-HCl pH. 7.4, 5 mM EDTA, 150 mM NaCl, 100 pM [$^{125}$I]-HEAT, membranes prepared from the alpha 1a cell line and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

EXAMPLE 16

Selective Binding Assays

Membranes prepared from stably transfected human alpha 1d and alpha 1b cell lines (ATCC CRL 11138 and CRL 11139, respectively) were used to identify compounds that selectively bind to the human alpha 1a adrenergic receptor. These competition binding reactions (total volume=200 µl) contained 50 mM Tris-HCl pH. 7.4, 5 mM EDTA, 150 mM NaCl, 100 pM [$^{125}$I]-HEAT, membranes prepared from cell lines transfected with the respective alpha 1 subtype expression plasmid and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

The compounds of the present invention prepared in the foregoing examples were found to have alpha 1a Ki values of less than about 20 nM as determined via the screening assay described in Example 15. All of the compounds were further found to be at least about 15-fold more selective in binding to alpha Ia receptors versus binding to the alpha 1b and alpha 1d receptors, as determined via the selective binding assay described in the preceding paragraph.

EXAMPLE 17

Counterscreen: Histamine-1 Selectivity

The binding affinity (Ki in nM) of the compounds of the present invention for histamine HI receptors can determined via the binding assay described in Chang et al., *J. Neurochem.* (1979), 32: 1653, or as described in U.S. Pat. No. 5,403,847, or suitable modifications thereof known to those skilled in the art. The assay can be used to eliminate agents which specifically affect binding to hH1 receptors.

EXAMPLE 18

EXEMPLARY COUNTERSCREENS
1. Assay Title: Dopamine D2, D3, D4 in vitro Screen
   Objective of the Assay:
   The objective of this assay is to eliminate agents which specifically affect binding of [$^3$H] spiperone to cells expressing human dopamine receptors D2, D3 or D4.
   Method:
   Modified from VanTol et al., *Nature* (1991), 350: 610–613.
   Frozen pellets containing specific dopamine receptor subtypes stably expressed in clonal cell lines are lysed in 2 ml lysing buffer (10 mM Tris-HCl/5 mM Mg, pH 7.4). Pellets obtained after centrifuging these membranes (15' at 24,450 rpm) are resuspended in 50 mM Tris-HCl pH 7.4 containing EDTA, MgCl$_2$, KCl, NaCl, CaCl$_2$ and ascorbate to give a 1 Mg/nL suspension. The assay is initiated by adding 50–75 µg membranes in a total volume of 500 µl containing 0.2 nM [$^3$H]-spiperone. Non-specific binding is defined using 10 µM apomorphine. The assay is terminated after a 2 hour incubation at room temperature by rapid filtration over GF/B filters presoaked in 0.3% PEI, using 50 mM Tris-HCl pH 7.4.
2. Assay Title: Serotonin 5HT1a
   Objective of the Assay
   The objective of this assay is to eliminate agents which specifically affect binding to cloned human 5HT1a receptor.
   Method:
   Modified from Schelegel and Peroutka, *Biochemical Pharmacology* (1986), 35: 1943–1949.
   Mammalian cells expressing cloned human 5HT1a receptors are lysed in ice-cold 5 mM Tris-HCl, 2 mM EDTA (pH 7.4) and homogenized with a polytron homogenizer. The homogenate is centrifuged at 1000×g for 30', and then the supernatant is centrifuged again at 38,000×g for 30'. The binding assay contains 0.25 nM [$^3$H]8-OH-DPAT (8-hydroxy-2-dipropylamino-1,2,3,4-tetrahydronaphthalene) in 50 mM Tris-HCl, 4 mM CaCl$_2$ and 1 mg/ml ascorbate. Non-specific binding is defined using 10 µM propranolol. The assay is terminated after a 1 hour incubation at room temperature by rapid filtration over GF/Cfilters.

EXAMPLE 19

EXEMPLARY FUNCTIONAL ASSAYS

In order to confirm the specificity of compounds for the human alpha 1a adrenergic receptor and to define the biological activity of the compounds, the following functional tests may be performed:
1. In vitro Rat, Dog and Human Prostate and Dog Urethra
   Taconic Farms Sprague-Dawley male rats, weighing 250–400 grams are sacrificed by cervical dislocation under anesthesia (methohexital; 50 mg/kg, i.p.). An incision is made into the lower abdomen to remove the ventral lobes of the prostate. Each prostate removed from a mongrel dog is cut into 6–8 pieces longitudinally along the urethra opening and stored in ice-cold oxygenated Krebs solution overnight before use if necessary. Dog urethra proximal to prostate is cut into approximately 5 mm rings, the rings are then cut open for contractile measurement of circular muscles. Human prostate chips from transurethral surgery of benign prostate hyperplasia are also stored overnight in ice-cold Krebs solution if needed.

The tissue is placed in a Petri dish containing oxygenated Krebs solution [NaCl, 118 mM; KCl, 4.7 mM; $CaCl_2$, 2.5 mM; $KH_2PO_4$, 1.2 mM; $MgSO_4$, 1.2 mM; $NaHCO_3$, 2.0 mM; dextrose, 11 mM] warmed to 37° C. Excess lipid material and connective tissue are carefully removed. Tissue segments are attached to glass tissue holders with 4-0 surgical silk and placed in a 5 ml jacketed tissue bath containing Krebs buffer at 37° C., bubbled with 5% $CO_2$/95% $O_2$. The tissues are connected to a Statham-Gould force transducer; 1 gram (rat, human) or 1.5 gram (dog) of tension is applied and the tissues are allowed to equilibrate for one hour. Contractions are recorded on a Hewlett-Packard 7700 series strip chart recorder.

After a single priming dose of 3 $\mu$M (for rat), 10 $\mu$M (for dog) and 20 $\mu$M (for human) of phenylephrine, a cumulative concentration response curve to an agonist is generated; the tissues are washed every 10 minutes for one hour. Vehicle or antagonist is added to the bath and allowed to incubate for one hour, then another cumulative concentration response curve to the agonist is generated.

$EC_5O$ values are calculated for each group using Graph-Pad Inplot software. pA2 (-log $K_b$) values were obtained from Schild plot when three or more concentrations were tested. When less than three concentrations of antagonist are tested, $K_b$ values are calculated according to the following formula $K_b$=[B];
x-1
where x is the ratio of $EC_{50}$ of agonist in the presence and absence of antagonist and [B] is the antagonist concentration.

2. Measurement of Intra-Urethral Pressure in Anesthetized Dogs

PURPOSE: Benign prostatic hyperplasia causes a decreased urine flow rate that may be produced by both passive physical obstruction of the prostatic urethra from increased prostate mass as well as active obstruction due to prostatic contraction. Alpha adrenergic receptor antagonists such as prazosin and terazosin prevent active prostatic contraction, thus improve urine flow rate and provide symptomatic relief in man. However, these are non-selective alpha 1 receptor antagonists which also have pronounced vascular effects. Because we have identified the alpha 1a receptor subtype as the predominent subtype in the human prostate, it is now possible to specifically target this receptor to inhibit prostatic contraction without concomitant changes in the vasculature. The following model is used to measure adrenergically mediated changes in intra-urethral pressure and arterial pressure in anesthetized dogs in order to evaluate the efficacy and potency of selective alpha adrenergic receptor antagonists. The goals are to: 1) identify the alpha-i receptor subtypes responsible for prostatic/urethral contraction and vascular responses, and 2) use this model to evaluate novel selective alpha adrenergic antagonists. Novel and standard alpha adrenergic antagonists may be evaluated in this manner.

METHODS: Male mongrel dogs (7–12 kg) are used in this study. The dogs are anesthetized with pentobarbital sodium (35 mg/kg, i.v. plus 4 mg/kg/hr iv infusion). An endotracheal tube is inserted and the animal ventilated with room air using a Harvard instruments positive displacement large animal ventilator. Catheters (PE 240 or 260) are placed in the aorta via the femoral artery and vena cava via the femoral veins (2 catheters, one in each vein) for the measurement of arterial pressure and the administration of drugs, respectively. A supra-pubic incision ~½ inch lateral to the penis is made to expose the urethers, bladder and urethra. The urethers are ligated and cannulated so that urine flows freely into beakers. The dome of the bladder is retracted to facilitate dissection of the proximal and distal urethra. Umbilical tape is passed beneath the urethra at the bladder neck and another piece of umbilical tape is placed under the distal urethra approximately 1–2 cm distal to the prostate. The bladder is incised and a Millar micro-tip pressure transducer is advanced into the urethra. The bladder incision is sutured with 2-0 or 3-0 silk (purse-string suture) to hold the transducer. The tip of the transducer is placed in the prostatic urethra and the position of the Millar catheter is verified by gently squeezing the prostate and noting the large change in urethral pressure.

Phenylephrine, an alpha 1 adrenergic agonist, is administered (0.1–100 ug/kg, iv; 0.05 ml/kg volume) in order to construct dose response curves for changes in intra-urethral and arterial pressure. Following administration of increasing doses of an alpha adrenergic antagonist (or vehicle), the effects of phenylephrine on arterial pressure and intra-urethral pressure are re-evaluated. Four or five phenylephrine dose-response curves are generated in each animal (one control, three or four doses of antagonist or vehicle). The relative antagonist potency on phenylephrine induced changes in arterial and intra-urethral pressure are determined by Schild analysis. The family of averaged curves are fit simultaneously (using ALLFIT software package) with a four paramenter logistic equation constraining the slope, minimum response, and maximum response to be constant among curves. The dose ratios for the antagonist doses (rightward shift in the dose-response curves from control) are calculated as the ratio of the $ED_{50}$'s for the respective curves. These dose-ratios are then used to construct a Schild plot and the Kb (expressed as ug/kg, iv) determined. The Kb (dose of antagonist causing a 2-fold rightward shift of the phenylephrine dose-response curve) is used to compare the relative potency of the antagonists on inhibiting phenylephrine responses for intra-urethral and arterial pressure. The relative selectivity is calculated as the ratio of arterial pressure and intra-urethral pressure Kb's. Effects of the alpha 1 antagonists on baseline arterial pressure are also monitored. Comparison of the relative antagonist potency on changes in arterial pressure and intra-urethral pressure provide insight as to whether the alpha receptor subtype responsible for increasing intra-urethral pressure is also present in the systemic vasculature. According to this method, one is able to confirm the selectivity of alpha 1a adrenergic receptor antagonists that prevent the increase in intra-urethral pressure to phenylephrine without any activity at the vasculature.

While the foregoing specification teaches the principles of the present invention, with examples provided for the purpose of illustration, the practice of the invention encompasses all of the usual variations, adaptations and/or modifications that come within the scope of the following claims.

What is claimed is:
1. A compound of formula:

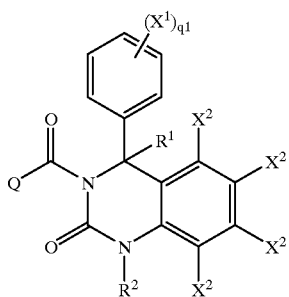

wherein Q is selected from the group consisting of:

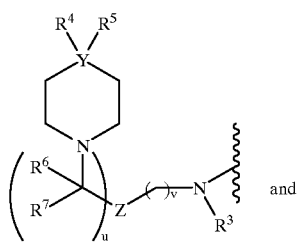 and

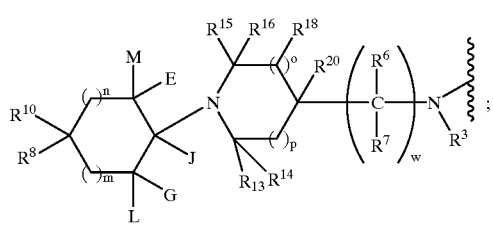

each $X^1$ is independently hydrogen, halogen, cyano, nitro, $C_1$–$C_8$ alkyl, $C_3$–$C_8$ cycloalkyl, fluorinated $C_1$–$C_8$ alkyl, fluorinated $C_3$–$C_8$ cycloalkyl, or $(CH_2)_{0-4}OR^a$;

each $X^2$ is independently hydrogen, halogen, cyano, nitro, $C_1$–$C_8$ alkyl, $C_3$–$C_8$ cycloalkyl, fluorinated $C_1$–$C_8$ alkyl, fluorinated $C_3$–$C_8$ cycloalkyl, or $(CH_2)_{0-4}OR^a$;

$R^1$ is hydrogen, $C_1$–$C_8$ alkyl, $C_3$–$C_8$ cycloalkyl, fluorinated $C_1$–$C_8$ alkyl, fluorinated $C_3$–$C_8$ cycloalkyl, phenyl, or substituted phenyl, wherein the substituents on the substituted phenyl are independently selected from halogen, cyano, nitro, $C_1$–$C_8$ alkyl, $C_3$–$C_8$ cycloalkyl, fluorinated $C_1$–$C_8$ alkyl, fluorinated $C_3$–$C_8$ cycloalkyl and $(CH_2)_{0-4}OR^a$;

$R^2$ is hydrogen, $C_1$–$C_8$ alkyl, or fluorinated $C_1$–$C_8$ alkyl;

$R^3$ is hydrogen, $C_1$–$C_8$ alkyl, or fluorinated $C_1$–$C_8$ alkyl;

Y is carbon or nitrogen, provided that when Y is nitrogen, $R^5$ is absent;

Z is $CH_2$, <u>CHOH</u>, $CHOR^b$, CHF, $CHR^b$, $C(R^b)_2$, $CF_2$, $CHCHF_2$, C=$CF_2$, or C=O;

E, G, L and M are each independently selected from hydrogen, $C_1$–$C_8$ alkyl, fluorinated $C_1$–$C_8$ alkyl, $C_3$–$C_8$ cycloalkyl, fluorinated $C_3$–$C_8$ cycloalkyl, $(CH_2)_{0-4}OR^c$, $(CH_2)_{0-4}N(R^c)_2$, $(CH_2)_{0-4}CN$, $(CH_2)_{0-4}CO_2R^c$, $(CH_2)_{0-4}CON(R^c)_2$, $(CH_2)_{0-4}SO_2R^c$ and $(CH_2)_{0-4}SO_2N(R^c)_2$;

J is hydrogen, $C_1$–$C_8$ alkyl, fluorinated $C_1$–$C_8$ alkyl, $C_3$–$C_8$ cycloalkyl, fluorinated $C_3$–$C_8$ cycloalkyl, $(CH_2)_{1-4}OR^c$, $(CH_2)_{1-4}N(R^c)_2$, $(CH_2)_{1-4}CN$, $(CH_2)_{0-4}CO_2R^c$, $(CH_2)_{0-4}CON(R^c)_2$, $(CH_2)_{0-4}SO_2R^c$, or $(CH_2)_{0-4}SO_2N(R^c)_2$;

$R^4$ is phenyl, substituted phenyl, naphthyl, substituted naphthyl, pyridyl, thienyl, furanyl, substituted pyridyl, substituted thienyl, or substituted furanyl; wherein the substituents on the substituted phenyl are independently selected from halogen, cyano, $OR^c$, $(CH_2)_{0-3}CON(R^c)_2$, $(CH_2)_{0-3}CO_2R^c$, methylenedioxy when the phenyl ring is di-substituted and the substituents are on adjacent carbon atoms, $C_1$–$C_4$ alkyl and fluorinated $C_1$–$C_4$ alkyl; and wherein the substituents on the substituted naphthyl, pyridyl, thienyl, or furanyl are independently selected from phenyl, $OR^c$, halogen, $C_1$–$C_4$ alkyl, fluorinated $C_1$–$C_4$ alkyl, $C_3$–$C_8$ cycloalkyl and fluorinated $C_3$–$C_8$ cycloalkyl;

$R^5$ is hydrogen, cyano, $OR^c$, $CO_2R^c$, $CON(R^c)_2$, tetrazole, isooxadiazole, phenyl, or substituted phenyl; wherein the substituents on the substituted phenyl are independently selected from halogen, cyano, $(CH_2)_{0-3}CON(R^c)_2$, $(CH_2)_{0-3}CO_2R^c$, <u>$OR^c$</u>, methylenedioxy when the phenyl ring is di-substituted and the substituents are on adjacent carbon atoms, $C_1$–$C_4$ alkyl and fluorinated $C_1$–$C_4$ alkyl;

$R^6$ and $R^7$ are each independently selected from hydrogen, $C_1$–$C_8$ alkyl, $C_3$–$C_8$ cycloalkyl, fluorinated $C_1$–$C_8$ alkyl and fluorinated $C_3$–$C_8$ cycloalkyl;

$R^8$ is phenyl, substituted phenyl, naphthyl, substituted naphthyl, pyridyl, substituted pyridyl, pyridyl N-oxide (N→O), substituted pyridyl N-oxide, pyrazinyl, substituted pyrazinyl, thienyl, substituted thienyl, thiazolyl, substituted thiazolyl, furanyl, substituted furanyl, quinazolinyl, or substituted quinazolinyl; wherein the substituents on the phenyl are independently selected from halogen, cyano, nitro, $OR^c$, $N(R^c)_2$, $NR^cCOR^c$, $NR^cCON(R^c)_2$, $NR^cSO_2R^c$, $NR^cSO_2N(R^c)_2$, $(CH_2)_{0-4}CO_2R^c$, $(CH_2)_{0-4}CON(R^c)_2$, $(CH_2)_{0-4}SO_2N(R^c)_2$, $(CH_2)_{0-4}SO_2R^c$, $C_{1-4}$ alkyl and fluorinated $C_1$–$C_4$ alkyl; and wherein the substituents on the substituted naphthyl, pyridyl, pyrazinyl, thienyl, thiazolyl, furanyl, or quinazolinyl are independently selected from cyano, nitro, $N(R^c)_2$, $(CH_2)_{0-4}CO_2R^c$, $(CH_2)_{0-4}CON(R^c)_2$, $(CH_2)_{0-4}SO_2N(R^c)_2$, $(CH_2)_{0-4}SO_2R^c$, phenyl, $OR^c$, halogen, $C_1$–$C_4$ alkyl, fluorinated $C_1$–$C_4$ alkyl, $C_3$–$C_8$ cycloalkyl and fluorinated $C_3$–$C_8$ cycloalkyl;

$R^{10}$ is hydrogen, cyano, $OR^c$, $CO_2R^c$, $CON(R^c)_2$, tetrazole, isooxadiazole, phenyl, substituted phenyl, naphthyl, substituted naphthyl, pyridyl, substituted pyridyl, thienyl, substituted thienyl, furanyl, or substituted furanyl; wherein the substituents on the substituted phenyl are independently selected from halogen, cyano, nitro, $OR^c$, $(CH_2)_{0-4}CO_2R^c$, $(CH_2)_{0-4}CON(R^c)_2$, $N(R^c)_2$, $NR^cCOR^c$, $NR^cCON(R^c)_2$, $NR^cSO_2R^c$, $NR^cSO_2N(R^c)_2$, $(CH_2)_{0-4}SO_2N(R^c)_2$, $(CH_2)_{0-4}SO_2R^c$, $C_1$–$C_4$ alkyl and fluorinated $C_1$–$C_4$ alkyl; and wherein the substituents on the substituted naphthyl, pyridyl, thienyl, or furanyl are independently selected from $(CH_2)_{0-4}CO_2R^c$, $(CH_2)_{0-4}CON(R^c)_2$, $(CH_2)_{0-4}SO_2N(R^c)_2$, $(CH_2)_{0-4}SO_2R^c$, phenyl, $OR^c$, halogen, $C_1$–$C_4$ alkyl, fluorinated $C_1$–$C_4$ alkyl and $C_3$–$C_8$ cycloalkyl;

$R^{13}$, $R^{14}$, $R^{15}$ and $R^{16}$ are each independently selected from hydrogen, $C_1$–$C_8$ alkyl, fluorinated $C_1$–$C_8$ alkyl, $C_3$–$C_8$ cycloalkyl, fluorinated $C_3$–$C_8$ cycloalkyl, and $(CH_2)_{2-4}OR^c$;

$R^{18}$ and $R^{20}$ are each independently selected from hydrogen and $OR^d$;

$R^a$ is hydrogen, $C_1$–$C_8$ alkyl, fluorinated $C_1$–$C_8$ alkyl, or $C_3$–$C_8$ cycloalkyl;

$R^b$ is $C_1$–$C_8$ alkyl, fluorinated $C_1$–$C_8$ alkyl, $C_3$–$C_8$ cycloalkyl, or fluorinated $C_3$–$C_8$ cycloalkyl;

$R^c$ is hydrogen, $C_1$–$C_8$ alkyl, fluorinated $C_1$–$C_8$ alkyl, $C_3$–$C_8$ cycloalkyl, or fluorinated $C_3$–$C_8$ cycloalkyl;

$R^d$ is hydrogen, $C_1$–$C_8$ alkyl, $C_3$–$C_8$ cycloalkyl, or $(CH_2)_{0-4}CF_3$;

m, n, o, and p are each independently integers from 0 to 3;

q1 is an integer from 0 to 5;

u and v are each independently integers from 0 to 3; provided that u and v are not both zero; and further provided that when u=0, Z is selected from $CH_2$, CHF, $CHR^b$, $C(R^b)_2$, $CF_2$, $CHCHF_2$ and $C=CF_2$; and w is an integer from 0 to 3, provided that when w is 0, $R^{20}$ is hydrogen;

or a pharmaceutically acceptable salt thereof.

2. The compound according to claim 1, wherein each $X^1$ is independently hydrogen, halogen, cyano, $C_1$–$C_4$ alkyl, $C_3$–$C_6$ cycloalkyl, fluorinated $C_1$–$C_4$ alkyl, fluorinated $C_3$–$C_6$ cycloalkyl, or $(CH_2)_{0-4}OR^a$;

each $X^2$ is independently hydrogen, halogen, cyano, $C_1$–$C_4$ alkyl, $C_3$–$C_6$ cycloalkyl, fluorinated $C_1$–$C_4$ alkyl, fluorinated $C_3$–$C_6$ cycloalkyl, or $(CH_2)_{0-4}OR^a$;

$R^1$ is hydrogen, $C_1$–$C_4$ alkyl, $C_3$–$C_6$ cycloalkyl, fluorinated $C_1$–$C_4$ alkyl, fluorinated $C_3$–$C_6$ cycloalkyl, phenyl, or substituted phenyl, wherein the substituents on the substituted phenyl are independently selected from halogen, cyano, $C_1$–$C_4$ alkyl, fluorinated $C_1$–$C_4$ alkyl and $(CH_2)_{0-4}OR^a$;

$R^2$ is hydrogen or $C_1$–$C_4$ alkyl;

$R^3$ is hydrogen or $C_1$–$C_4$ alkyl;

E, G, L and M are each independently selected from hydrogen and $C_1$–$C_4$ alkyl;

J is hydrogen or $C_1$–$C_4$ alkyl;

$R^4$ is phenyl, mono- or di- or tri-substituted phenyl, pyridyl, thienyl, or furanyl; wherein the substituents on the substituted phenyl are independently selected from halogen, cyano, $CO_2R^c$, $OR^c$, $CON(R^c)_2$, methylenedioxy, $C_1$–$C_4$ alkyl and fluorinated $C_1$–$C_4$ alkyl;

$R^5$ is hydrogen, cyano, $OR^c$, $CO_2R^c$, $CON(R^c)_2$, phenyl, or mono- or di- or tri-substituted phenyl, wherein the substituents on the substituted phenyl are independently selected from halogen, cyano, $CO_2R^c$, $OR^c$, $CON(R^c)_2$, methylenedioxy, $C_1$–$C_4$ alkyl and fluorinated $C_1$–$C_4$ alkyl;

one of $R^6$ and $R^7$ is hydrogen, and the other of $R^6$ and $R^7$ is hydrogen or $C_1$–$C_4$ alkyl;

$R^8$ is phenyl, mono- or di- or tri-substituted phenyl, pyridyl, or mono- or di- or tri-substituted pyridyl; wherein the substituents on the phenyl are independently selected from halogen, cyano, $OR^c$, $N(R^c)_2$, $NR^cCOR^c$, $NR^cCON(R^c)_2$, $NR^cSO_2R^c$, $NR^cSO_2N(R^c)_2$, $(CH_2)_{0-4}CO_2R^c$, $(CH_2)_{0-4}CON(R^c)_2$, $(CH_2)_{0-4}SO_2N(R^c)_2$, $(CH_2)_{0-4}SO_2R^c$, $C_{1-4}$ alkyl and $CF_3$; and wherein the substituents on the substituted pyridyl are independently selected from cyano, nitro, $N(R^c)_2$, $(CH_2)_{0-4}CO_2R^c$, $(CH_2)_{0-4}CON(R^c)_2$, $(CH_2)_{0-4}SO_2N(R^c)_2$, $(CH_2)_{0-4}SO_2R^c$, phenyl, $OR^c$, halogen, $C_1$–$C_4$ alkyl and $CF_3$;

$R^{10}$ is hydrogen, cyano, $OR^c$, $CO_2R^c$, $CON(R^c)_2$, phenyl, or mono- or di- or tri-substituted phenyl wherein the substituents on the phenyl are independently selected from halogen, cyano, $OR^c$, $(CH_2)_{0-4}CO_2R^c$, $(CH_2)_{0-4}CON(R^c)_2$, $N(R^c)_2$, $NR^cCOR^c$, $NR^cCON(R^c)_2$, $NR^cSO_2R^c$, $NR^cSO_2N(R^c)_2$, $(CH_2)_{0-4}SO_2N(R^c)_2$, $(CH_2)_{0-4}SO_2R^c$ and $C_1$–$C_4$ alkyl;

$R^{13}$, $R^{14}$, $R^{15}$ and $R^{16}$ are each independently selected from hydrogen and $C_1$–$C_4$ alkyl;

$R^a$ is hydrogen, $C_1$–$C_4$ alkyl, or $(CH_2)_{0-3}CF_3$;

$R^b$ is $C_1$–$C_4$ alkyl or $(CH_2)_{0-3}CF_3$;

$R^c$ is hydrogen, $C_1$–$C_4$ alkyl, or $(CH_2)_{0-3}CF_3$;

$R^d$ is hydrogen, $C_1$–$C_4$ alkyl, or $(CH_2)_{0-3}CF_3$;

m, n, o, and p are each independently 0 or 1; and q1 is an integer from 0 to 4;

or a pharmaceutically acceptable salt thereof.

3. The compound according to claim 1, wherein Q is

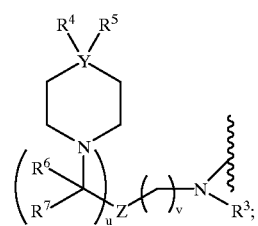

each $X^1$ is independently hydrogen, halogen, cyano, $C_1$–$C_4$ alkyl, $C_3$–$C_6$ cycloalkyl, fluorinated $C_1$–$C_4$ alkyl, fluorinated $C_3$–$C_6$ cycloalkyl, or $(CH_2)_{0-4}OR^a$;

each $X^2$ is independently hydrogen, halogen, cyano, $C_1$–$C_4$ alkyl, $C_3$–$C_6$ cycloalkyl, fluorinated $C_1$–$C_4$ alkyl, fluorinated $C_3$–$C_6$ cycloalkyl, or $(CH_2)_{0-4}OR^a$;

$R^1$ is hydrogen, $C_1$–$C_4$ alkyl, $C_3$–$C_6$ cycloalkyl, fluorinated $C_1$–$C_4$ alkyl, fluorinated $C_3$–$C_6$ cycloalkyl, phenyl, or substituted phenyl, wherein the substituents on the substituted phenyl are independently selected from halogen, cyano, $C_1$–$C_4$ alkyl, fluorinated $C_1$–$C_4$ alkyl and $(CH_2)_{0-4}OR^a$;

$R^2$ is hydrogen or $C_1$–$C_4$ alkyl;

$R^3$ is hydrogen or $C_1$–$C_4$ alkyl;

$R^4$ is phenyl, mono- or di- or tri-substituted phenyl, pyridyl, thienyl, or furanyl; wherein the substituents on the substituted phenyl are independently selected from halogen, cyano, $CO_2R^c$, $OR^c$, $CON(R^c)_2$, methylenedioxy, $C_1$–$C_4$ alkyl and fluorinated $C_1$–$C_4$ alkyl;

$R^5$ is hydrogen, cyano, $OR^c$, $CO_2R^c$, $CON(R^c)_2$, phenyl, or mono- or di- or tri-substituted phenyl, wherein the substituents on the substituted phenyl are independently selected from halogen, cyano, $CO_2R^c$, $OR^c$, $CON(R^c)_2$, methylenedioxy, $C_1$–$C_4$ alkyl and fluorinated $C_1$–$C_4$ alkyl;

one of $R^6$ and $R^7$ is hydrogen, and the other of $R^6$ and $R^7$ is hydrogen or $C_1$–$C_4$ alkyl;

$R^a$ is hydrogen, $C_1$–$C_4$ alkyl, or $(CH_2)_{0-3}CF_3$;

$R^b$ is $C_1$–$C_4$ alkyl or $(CH_2)_{0-3}CF_3$;

$R^c$ is hydrogen, $C_1$–$C_4$ alkyl, or $(CH_2)_{0-3}CF_3$; and q1 is an integer from 0 to 4;

or a pharmaceutically acceptable salt thereof.

4. The compound according to claim 3, having the formula:

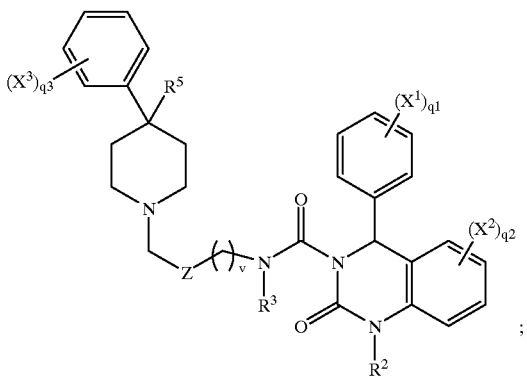

wherein Z is $CH_2$, CHOH or C=O;

each $X^3$ is independently hydrogen, $CF_3$, cyano, halogen, or $C_1-C_4$ alkyl;

$R^5$ is hydrogen, cyano, or $CO_2R^c$;

q2 is an integer from 0 to 4; and q3 is an integer from 0 to 3;

or a pharmaceutically acceptable salt thereof.

5. The compound according to claim 4, having the formula:

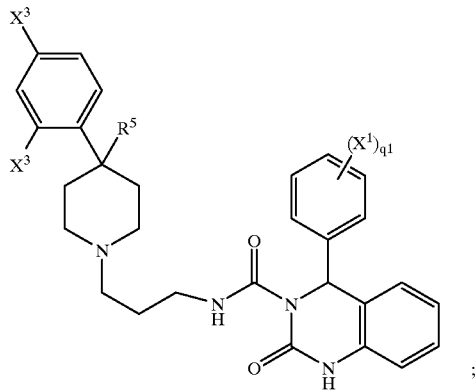

wherein each $X^1$ is independently hydrogen, fluorine, methyl, ethyl, cyano, $CF_3$, methoxy, ethoxy, or $OCF_3$;

each $X^3$ is independently hydrogen, $CF_3$, cyano, fluorine, methyl, or ethyl; and q1 is an integer from 0 to 2;

or a pharmaceutically acceptable salt thereof.

6. The compound according to claim 5, selected from the group consisting of 4-(3,4-difluorophenyl)-3-((4-cyano-4-(2-cyanophenyl)piperidin-1-yl)propylcarbamoyl)-3,4-dihydro-quinazolin-2-one;

4-(3,4-difluorophenyl)-3-((4-(4-fluorophenyl)piperidin-1-yl)propylcarbamoyl)-3,4-dihydro-quinazolin-2-one;

and pharmaceutically acceptable salts thereof.

7. The compound according to claim 1, wherein Q is

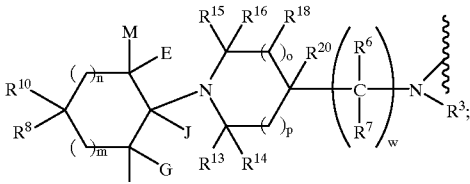

each $X^1$ is independently hydrogen, halogen, cyano, $C_1-C_4$ alkyl, $C_3-C_6$ cycloalkyl, fluorinated $C_1-C_4$ alkyl, fluorinated $C_3-C_6$ cycloalkyl, or $(CH_2)_{0-4}OR^a$;

each $X^2$ is independently hydrogen, halogen, cyano, $C_1-C_4$ alkyl, $C_3-C_6$ cycloalkyl, fluorinated $C_1-C_4$ alkyl, fluorinated $C_3-C_6$ cycloalkyl, or $(CH_2)_{0-4}OR^a$;

$R^1$ is hydrogen, $C_1-C_4$ alkyl, $C_3-C_6$ cycloalkyl, fluorinated $C_1-C_4$ alkyl, fluorinated $C_3-C_6$ cycloalkyl, phenyl, or substituted phenyl, wherein the substituents on the substituted phenyl are independently selected from halogen, cyano, $C_1-C_4$ alkyl, fluorinated $C_1-C_4$ alkyl and $(CH_2)_{0-4}OR^a$;

$R^2$ is hydrogen or $C_1-C_4$ alkyl;

$R^3$ is hydrogen or $C_1-C_4$ alkyl;

E, G, L and M are each independently selected from hydrogen and $C_1-C_4$ alkyl;

J is hydrogen or $C_1-C_4$ alkyl;

one of $R^6$ and $R^7$ is hydrogen, and the other of $R^6$ and $R^7$ is hydrogen or $C_1-C_4$ alkyl;

$R^8$ is selected from phenyl, mono- or di- or tri-substituted phenyl, pyridyl, or mono- or di- or tri-substituted pyridyl; wherein the substituents on the phenyl are independently selected from halogen, cyano, $OR^c$, $N(R^c)_2$, $NR^cCOR^c$, $NR^cCON(R^c)_2$, $NR^cSO_2R^c$, $NR^cSO_2N(R^c)_2$, $(CH_2)_{0-4}CO_2R^c$, $(CH_2)_{0-4}CON(R^c)_2$, $(CH_2)_{0-4}SO_2N(R^c)_2$, $(CH_2)_{0-4}SO_2R^c$, $C_{1-4}$ alkyl and $CF_3$; and wherein the substituents on the substituted pyridyl are independently selected from cyano, $N(R^c)_2$, $(CH_2)_{0-4}CO_2R^c$, $(CH_2)_{0-4}CON(R^c)_2$, $(CH_2)_{0-4}SO_2N(R^c)_2$, $(CH_2)_{0-4}SO_2R^c$, phenyl, $OR^c$, halogen, $C_1-C_4$ alkyl and $CF_3$;

$R^{10}$ is hydrogen, cyano, $OR^c$, $CO_2R^c$, $CON(R^c)_2$, phenyl, or mono- or di- or tri-substituted phenyl, wherein the substituents on the phenyl are independently selected from halogen, cyano, $OR^c$, $(CH_2)_{0-4}CO_2R^c$, $(CH_2)_{0-4}CON(R^c)_2$, $N(R^c)_2$, $NR^cCOR^c$, $NR^cCON(R^c)_2$, $NR^cSO_2R^c$, $NR^cSO_2N(R^c)_2$, $(CH_2)_{0-4}SO_2N(R^c)_2$, $(CH_2)_{0-4}SO_2R^c$ and $C_1-C_4$ alkyl;

$R^{13}$, $R^{14}$, $R^{15}$ and $R^{16}$ are each independently selected from hydrogen and $C_1-C_4$ alkyl;

$R^a$ is hydrogen, $C_1-C_4$ alkyl, or $(CH_2)_{0-3}CF_3$;

$R^c$ is hydrogen, $C_1-C_4$ alkyl, or $(CH_2)_{0-3}CF_3$;

$R^d$ is hydrogen, $C_1-C_4$ alkyl, or $(CH_2)_{0-4}CF_3$;

m, n, o, and p are each independently 0 or 1; and q1 is an integer from 0 to 4;

or a pharmaceutically acceptable salt thereof.

8. The compound according to claim 7, having the formula:

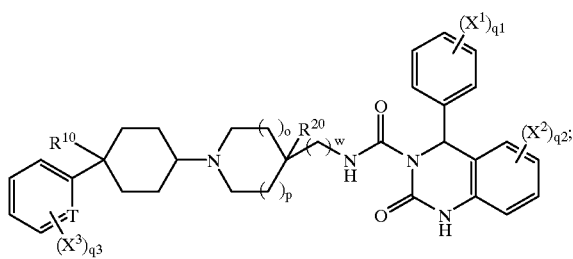

wherein T is C—$X^3$ or N;

each $X^3$ is independently hydrogen, halogen, cyano, $OR^c$, $CO_2R^c$, $CON(R^c)_2$, $SO_2N(R^c)_2$, $SO_2R^c$, $C_{1-4}$ alkyl, or $CF_3$;

$R^{10}$ is hydrogen, cyano, or $OR^c$;

$R^{20}$ is hydrogen or OH;

q2 is an integer from 0 to 4;

q3 is an integer from 0 to 3; and w is 0 or 1, provided that when w is 0, $R^{20}$ is hydrogen;

or a pharmaceutically acceptable salt thereof.

9. The compound according to claim 8, wherein each $X^1$ is fluorine;

each $X^2$ is hydrogen;

$R^{20}$ is hydrogen;

q1 is an integer from 0 to 3; and w is 1;

or a pharmaceutically acceptable salt thereof.

10. The compound according to claim 9, selected from the group consisting of trans-4-(3,4-difluorophenyl)-3-((1-(4-(2-cyanophenyl) cyclohexyl)-3-hydroxy-azetidin-3-yl) methylcarbamoyl)-3,4-dihydro-quinazolin-2-one;

trans-4-(3,4-difluorophenyl)-3-((1-(4-(2-cyanophenyl) cyclohexyl)azetidin-3-yl)methylcarbamoyl)-3,4-dihydro-quinazolin-2-one;

trans-4-(3,4-difluorophenyl)-3-((1-(4-(2-pyridyl) cyclohexyl)azetidin-3-yl)methylcarbamoyl)-3,4-dihydro-quinazolin-2(3H)-one;

and pharmaceutically acceptable salts thereof.

11. A pharmaceutical composition comprising the compound according to claim 1 and a pharmaceutically acceptable carrier.

12. A pharmaceutical composition made by combining the compound according to claim 1 and a pharmaceutically acceptable carrier.

13. A process for making a pharmaceutical composition comprising combining the compound according to claim 1 and a pharmaceutically acceptable carrier.

14. The composition according to claim 11 further comprising a testosterone 5-alpha reductase inhibitor.

15. The composition according to claim 14, wherein the testosterone 5-alpha reductase inhibitor is a type 1, a type 2, both a type 1 and a type 2, or a dual type 1 and type 2 testosterone 5-alpha reductase inhibitor.

16. The composition according to claim 15, wherein the testosterone 5-alpha reductase inhibitor is a type 2 testosterone 5-alpha reductase inhibitor.

17. The composition according to claim 16, wherein the testosterone 5-alpha reductase inhibitor is finasteride.

18. A method of treating benign prostatic hyperplasia in a subject in need thereof which comprises administering to the subject a therapeutically effective amount of the compound according to claim 1.

19. The method according to claim 18, wherein the compound does not cause a fall in blood pressure at dosages effective to alleviate benign prostatic hyperlasia.

20. The method according to claim 18, wherein the compound is administered in combination with a testosterone 5-alpha reductase inhibitor.

21. The method according to claim 20, wherein the testosterone 5-alpha reductase inhibitor is finasteride.

22. A method of treating benign prostatic hyperplasia in a subject in need thereof which comprises administering a therapeutically effective amount of the composition according to claim 11.

23. The method according to claim 22, wherein the composition further comprises a therapeutically effective amount of a testosterone 5-alpha reductase inhibitor.

24. A method of relaxing lower urinary tract tissue in a subject in need thereof which comprises administering to the subject a therapeutically effective amount of the compound according to claim 1.

25. The method according to claim 24, wherein the compound is administered in combination with a testosterone 5-alpha reductase inhibitor.

26. The method according to claim 25, wherein the testosterone 5-alpha reductase inhibitor is finasteride.

27. A method of treating a condition which is susceptible to treatment by antagonism of the alpha 1a receptor which comprises administering to a subject in need thereof an amount of the compound according to claim 1 effective to treat the condition.

28. A method of eliciting an alpha 1a antagonizing effect in a mammal in need thereof, comprising administering to the mammal a therapeutically effective amount of the compound according to claim 1.

* * * * *